(12) United States Patent
Vogt et al.

(10) Patent No.: US 10,864,314 B2
(45) Date of Patent: Dec. 15, 2020

(54) KNEE SPACER SYSTEM WITH IRRIGATION DEVICE

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

( * ) Notice: Subject to any disclaimer, the term of this patent is extended or adjusted under 35 U.S.C. 154(b) by 82 days.

(21) Appl. No.: 16/359,471

(22) Filed: Mar. 20, 2019

(65) Prior Publication Data

US 2019/0290834 A1 Sep. 26, 2019

(30) Foreign Application Priority Data

Mar. 21, 2018 (DE) .......... 10 2018 106 704

(51) Int. Cl.
| | |
|---|---|
| *A61F 2/38* | (2006.01) |
| *A61M 3/02* | (2006.01) |
| *A61F 2/46* | (2006.01) |
| *A61M 39/24* | (2006.01) |
| *A61F 2/30* | (2006.01) |
| *A61M 25/00* | (2006.01) |

(52) U.S. Cl.
CPC .......... *A61M 3/0283* (2013.01); *A61F 2/389* (2013.01); *A61F 2/3859* (2013.01); *A61F 2/4684* (2013.01); *A61M 39/24* (2013.01); *A61F 2/4675* (2013.01); *A61F 2002/3068* (2013.01); *A61F 2002/30672* (2013.01); *A61F 2002/30677* (2013.01); *A61F 2002/30691* (2013.01); *A61F 2002/30784* (2013.01); *A61F 2002/30878* (2013.01); *A61F 2002/4615* (2013.01); *A61F 2002/4631* (2013.01); *A61M 25/0097* (2013.01); *A61M 2039/248* (2013.01); *A61M 2039/2433* (2013.01); *A61M 2205/04* (2013.01)

(58) Field of Classification Search
CPC .......... A61F 2/38; A61F 2/389; A61M 3/0283
See application file for complete search history.

(56) References Cited

U.S. PATENT DOCUMENTS

| | | |
|---|---|---|
| 4,880,006 A | 11/1989 | Albrektsson et al. |
| 8,562,687 B2 | 10/2013 | Faccioli et al. |
| 9,839,523 B1 | 12/2017 | Foran |
| 2013/0324931 A1 | 12/2013 | Meridew et al. |
| 2014/0128833 A1 | 5/2014 | Vogt |
| 2014/0288659 A1 | 9/2014 | Vogt |
| 2014/0343560 A1 | 11/2014 | Vogt |
| 2015/0018832 A1 | 1/2015 | Vogt |

(Continued)

FOREIGN PATENT DOCUMENTS

| | | |
|---|---|---|
| EP | 2740468 | 6/2014 |
| EP | 2758004 | 7/2014 |

(Continued)

*Primary Examiner* — Matthew W Schall
(74) *Attorney, Agent, or Firm* — Stradley Ronon Stevens & Young, LLP

(57) ABSTRACT

Disclosed herein is a temporary knee spacer system for the temporary replacement of a knee joint, which is designed for the interim phase of two-stage septic revisions of knee joint total endoprostheses. The knee spacer system can be used in particular with two-phase septic revisions with which two or more microbial germs are the cause of an infection of the knee joint total endoprosthesis and the surrounding tissue.

29 Claims, 15 Drawing Sheets

(56) References Cited

U.S. PATENT DOCUMENTS

| | | |
|---|---|---|
| 2017/0312087 A1 | 11/2017 | Faccioli et al. |
| 2018/0008423 A1 | 1/2018 | Foran |

FOREIGN PATENT DOCUMENTS

| | | |
|---|---|---|
| EP | 2781206 | 9/2014 |
| EP | 2826445 | 1/2015 |
| EP | 3170476 A1 | 5/2017 |
| EP | 1971293 | 9/2018 |
| WO | 2017098316 | 6/2017 |
| WO | 2017199131 | 11/2017 |
| WO | 2017213852 | 12/2017 |

KNEE SPACER SYSTEM WITH IRRIGATION DEVICE

CROSS-REFERENCE TO RELATED APPLICATIONS

This application claims the benefit of priority under 35 U.S.C. § 119(a) to patent application DE 10 2018 106 704.6, filed on Mar. 21, 2018, the contents of which are incorporated herein by reference.

BACKGROUND

Disclosed herein is a temporary knee spacer system for the temporary replacement of a knee joint, which is designed for the interim phase of two-stage septic revisions of knee joint total endoprostheses. The knee spacer system can be used in particular with two-phase septic revisions with which two or more microbial germs are the cause of an infection of the knee joint total endoprosthesis and the surrounding tissue.

Knee joint total endoprostheses are implanted worldwide on a large scale. The durability of these implants is currently approximately 15 years. Unfortunately, it can occur with a small percentage that knee joint total endoprostheses are infected with microbial germs, particularly gram-positive bacteria, as well as gram-negative bacteria, and to a very low degree with yeasts and fungi. These microbial germs, mainly typical skin germs such as *Staphylococcus aureus* and *Staphylococcus epidermidis*, can enter the patient during a surgical operation (OP). Additionally, it is also possible that microbial germs reach hematogenic knee joint total endoprostheses. When knee joint endoprostheses are infected with microbial germs, the surrounding bone and soft tissue is also infected and is damaged by the microbial germs.

The prior art is predominantly two treatment methods for infected knee joint total endoprostheses: single-stage septic revision and two-stage septic revision. Additionally, there are also a number of further treatment methods, such as the use of suction-rinse drainage procedures.

With single-stage revision, the infected knee joint total endoprosthesis is first removed during an OP, then the area is radically debrided, and then a revision knee joint endoprosthesis is implanted.

With two-stage septic revisions, in a first OP, the infected knee joint total endoprosthesis is first removed, then the area is debrided and then a knee joint spacer is implanted. A tibia component and a femur component of the knee joint spacer are anchored on the tibia or on the femur with bone cement. The knee joint spacer remains in the patient for up to several weeks until the infection has subsided and the clinical infection markers have decreased. Then, in a second OP, the knee joint spacer is removed and after renewed debridement, a revision knee joint endoprosthesis is implanted.

The use of spacers equipped with antibiotics is known. These spacers can on the one hand be produced by the OP staff during the OP itself from PMMA bone cement powder, antibiotics and monomer fluid, and on the other, it is also common to use industrially produced spacers made of bone cement.

With the spacers used to date, antibiotics are added to the bone cement before the spacer is actually produced. With this antibiotically modified bone cement powder, the spacers are then poured, which then harden through polymerization with the aid of a monomer fluid added to the cement powder. The bone cement paste here essentially encloses the antibiotics. Only the antibiotic particles in the areas close to the surface are released due to the effect of bodily fluids. The release of the active substances is highest at first, and then decreases during the course of several days. Then, only small quantities of the antibiotics are released. The main quantity of the added antibiotics remains in the hardened bone cement of the spacer. A subsequent change to the type and number of the antibiotics used is not possible after production of the spacer or after implantation with the spacers produced to date from bone cement. Further, the adjustment of a defined concentration of antimicrobial active substances in the wound secretion or the body fluid surrounding the spacer components is also not possible.

Industrially prefabricated knee joint spacers that contain one or two antibiotics are known from a series of documents. Examples of these are patent application WO 2017/199 131 A1 and patents EP 2 758 004 B1, U.S. Pat. No. 8,562,687 B2, EP 2 781 206 B1 and EP 2 826 445 B1.

In patent EP 1 971 293 B1, a knee joint spacer is recommended that contains a reservoir for active substance solutions with a pump mechanism. The pump mechanism is actuated by a walking movement of the patient and pumps the active substance solution from the reservoir. In principle, this is a membrane pump.

In patent EP 2 740 468 B1, an implant is disclosed that contains capillaries that can be filled with active substance solutions. Further, the implant contains the metal magnesium on one end of the capillaries. In the presence of humidity, the magnesium corrodes. It disintegrates under the effect of water and releases hydrogen. This gas continuously drives the active substance solution out of the capillaries over a period of several days.

US 2018/0008423 A1 describes a knee joint spacer that can be used with infected knee joint total endoprostheses. Contrary to single-stage and two-stage septic revisions, the femur component and the tray of the knee component from the infected knee joint total endoprosthesis remain in the patient. Only the plastic inlay is removed and replaced by the spacer. The spacer re-forms the plastic inlay. This has the disadvantage that germs that have settled in other parts of the knee joint total endoprosthesis can only be reached with difficulty by the active substance from the spacer, if at all. The spacer is characterized by the fact that it contains a reservoir for holding antibiotic solutions. The antibiotic solutions are issued through proximal openings in the running surface of the spacer. The reservoir of the spacer can be re-filled via an access opening. For this purpose, the access opening is equipped with a port. The problem with such spacers is that fluid must be brought into the reservoir without a pressure compensation being possible. This means that with large fluid volumes and under high pressure during injection, the antibiotic fluid is under certain circumstances pressed into the soft tissue or into efferent blood vessels. A drainage of wound secretion and debris is not possible with this spacer.

With two-stage septic revision, drainage systems are also used with the implantation of the knee joint spacer that are designed for draining wound secretion, blood and debris. The drainage systems remain in the patient for up to several days. The antibiotic active substances released by the spacer components are taken up by the wound secretion and discharged outwards via the drainage. As a result, a portion of the antimicrobial active substances for protecting the spacer surface against microbial infection is lost.

It was recognized within the scope of the present invention that it would be desirable if the spacer surface could be surrounded by an antimicrobial active substance solution, the active substance concentration of which could be precisely adjusted, and the concentration of which could remain over several days, independently of the flow of wound secretion. Further, it would be desirable that the type and number of microbial active substances could also vary after the implantation of the knee joint spacer, in order to be able to react to microbial germs that are only detected later, for example. At the same time, the patient should be able to move the knee joint in order to prevent a shortening of the fascia and the muscles and a degeneration of the leg muscles, and thus a shortening of the rehabilitation process.

Objects

The object of the present invention is to overcome the disadvantages of the prior art. In particular, the object of the invention is to develop a temporary knee spacer system that enables improved and patient-specific applications. Preferably, a knee spacer system should be developed with which a medical irrigation fluid can be used in the area of the knee in a targeted manner. At the same time, the knee spacer system should enable mobility of the knee in the state in which it is inserted in the patient.

The object of the invention in particular is to develop an articulating knee spacer system which is designed for the interim phase of two-stage septic revisions of knee joint total endoprostheses. The knee spacer system should fill out the spacer after removal of the knee joint total endoprosthesis and the following debridement such that a degeneration of the ligamentous apparatus and the muscles is prevented. The knee spacer system to be developed should make it possible to rinse the articulating spacer surfaces, the soft tissue surrounding the spacer components, and at least a portion of the surrounding bone tissue, with an antiseptic or antibiotic irrigation fluid, continuously or discontinuously. Further, the knee spacer system should as far as possible be designed such that the irrigation fluid cannot leave the space around the knee spacer system in an uncontrolled manner. The knee spacer system should be connectable with the bone tissue of the tibia and the femur with bone cement in such a manner that the discharge of the irrigation fluid from the knee spacer system and also the take-up of the irrigation fluid into the knee spacer system for drainage is not hindered or interrupted. The knee spacer system should further as far as possible be designed such that after termination of the irrigation with the medical irrigation fluid, the irrigation fluid feed and the irrigation fluid discharge can be removed without an impairment of the articulation of the spacer components resulting.

SUMMARY

The objects of the invention are achieved by a temporary knee spacer system for the temporary replacement of a knee joint, the knee spacer system comprising:
A) tibia component, wherein the tibia component has a tibia prosthetic body, wherein the tibia prosthetic body has two running surfaces on a proximal side of the tibia component and at least one attachment surface for mounting the tibia component on a tibia on a distal side of the tibia prosthetic body; B) a first tubular and fluid-permeable connecting means for feeding a medical irrigation fluid into the tibia prosthetic body; C) a second tubular and fluid-permeable connecting means for draining a medical irrigation fluid from the tibia prosthetic body; D) an irrigation fluid inlet opening in a surface of the tibia prosthetic body, wherein the first connecting means is connected or connectable in a fluid-permeable manner to the irrigation fluid inlet opening; E) an irrigation fluid outlet opening in the surface of the tibia prosthetic body, wherein the second connecting means is connected or connectable in a fluid-permeable manner to the irrigation fluid outlet opening; F) at least one irrigation fluid exit opening in the surface of the tibia prosthetic body, which is connected in the interior of the tibia prosthetic body with the irrigation fluid inlet opening in a fluid-permeable manner; and G) at least one irrigation fluid entry opening in the surface of the tibia prosthetic body, which is connected in the interior of the prosthetic body with the irrigation fluid outlet opening in a fluid-permeable manner, whereby the at least one irrigation fluid exit opening and the at least one irrigation fluid entry opening are arranged outside the at least one mounting surface, and whereby the at least one irrigation fluid exit opening in the interior of the prosthetic body is not connected in a fluid-permeable manner with the irrigation fluid outlet opening and the at least one irrigation fluid entry opening in the interior of the prosthetic body is not connected with the irrigation fluid inlet opening in a fluid-permeable manner.

The knee spacer system according to the invention can therefore only have a tibia component and does not need any further parts, and therefore also no femur component. Preferably, the knee spacer system also has a femur component, however.

The irrigation fluid can theoretically also first be introduced via the first connecting means and discharged via the second connecting means, and then introduced via the second connecting means and discharged via the first connecting means. The prosthesis is then operated in alternation. However, it is preferred according to the invention that the prosthesis is only operated in a flow direction of the irrigation fluid.

Preferably, the first tubular fluid-permeable connecting means is a hose with an adapter or a connection and the second tubular fluid-permeable connecting means is also a hose with an adapter or a connection.

In the present patent application, the "proximal", "distal" and "lateral" directions and the "sagittal", "frontal" and "transverse" planes are used in relation to the knee spacer system in the manner in which this would be understood when inserted in the patient, as an anatomical direction or a physical plane. Here, "proximal" means towards the center of the body, and "distal" means away from the center of the body.

Preferably, it can be provided that the knee spacer system is suitable for the use of an antibiotic active substance, which prevents or impairs a polymerization or a radical polymerization of PMMA. In particular, it can be provided that the knee spacer system is suitable for the use of Rifampicin and Metronidazol.

It can also be provided according to the invention that the at least one mounting surface is bound or that the at least one mounting surface is bound by a surrounding ridge that rises from the surface of the tibia prosthetic body, so that the at least one mounting surface is suitable for holding bone cement paste within the ridge.

As a result, a bound and therefore determined area for mounting the tibia component can be used. When the knee spacer system is used correctly, it can be prevented that the first and second connecting means and the irrigation fluid inlet opening and the irrigation fluid outlet opening are covered with bone cement and as a result, their functioning is impaired. In particular, it can be prevented that the hardened bone cement prevents a pulling off or a loosening of the first and second connecting means from the tibia prosthetic body.

It is provided that the at least one irrigation fluid exit opening in the interior of the prosthetic body is not connected in a fluid-permeable manner with the irrigation fluid outlet opening and the at least one irrigation fluid entry opening in the interior of the prosthetic body is not connected with the irrigation fluid inlet opening in a fluid-permeable manner.

As a result, it is ensured that with the knee spacer system, a circuit with the irrigation fluid can be generated without the irrigation fluid first being pressed in and then having to be suctioned out. This is gentler in terms of the application. The knee spacer system can alternatively be used such that the irrigation fluid is first introduced into the knee spacer system and exits through the at least one irrigation fluid exit opening and the at least one irrigation fluid entry opening, and then the irrigation fluid is again suctioned out and here is suctioned back into the tibia prosthetic body through the at least one irrigation fluid outlet opening and the at least one irrigation fluid inlet opening. Preferably, however, a circuit with the irrigation fluid is generated.

According to a further preferred embodiment of the present invention, it can be provided that the tibia component has at least two irrigation fluid exit openings and at least two irrigation fluid entry openings in the surface of the tibia prosthetic body, which are arranged on different sides of the tibia prosthetic body, whereby preferably an irrigation fluid exit opening and an irrigation fluid entry opening are arranged on the proximal side of the tibia prosthetic body and an irrigation fluid exit opening and an irrigation fluid entry opening are arranged on the distal side of the tibia prosthetic body.

Thus, two separate circuits can be produced with the medical irrigation fluid, which run both on the distal and the proximal side of the inserted tibia component.

Further, it can be provided that the at least one irrigation fluid exit opening and the at least one irrigation fluid entry opening are spaced apart from each other in pairs, wherein the space between each pair of the at least one irrigation fluid exit opening and the at least one irrigation fluid entry opening is at least 5 mm, preferably at least 20 mm and particularly preferably, at least 30 mm.

As a result, it is ensured that the circuit of the medical irrigation fluid has to cover a longer distance (at least 5 mm) on the outer surface of the tibia prosthetic body and is there available for irrigation.

Additionally, it can be provided that the first connecting means on the side facing away from the connection with the irrigation fluid inlet opening and the second connecting means on the side facing away from the connection with the irrigation fluid outlet opening each has one adapter, in particular each has a Luer lock adapter.

As a result, the knee spacer system can be conveniently connected to a medical irrigation fluid reservoir with a pump and to a catch pan for capturing the used irrigation fluid.

Preferably, it can also be provided that at the irrigation fluid inlet opening in the interior of the tibia prosthetic body or on the surface of the tibia prosthetic body, a self-sealing coupling is arranged, and at the irrigation fluid outlet opening in the interior of the tibia prosthetic body or on the surface of the tibia prosthetic body, a self-sealing coupling is arranged, wherein the first connecting means is detachably connected or connectable with the irrigation fluid inlet opening and the second connecting means is detachably connected or connectable with the irrigation fluid outlet opening.

As a result, the irrigation fluid inlet opening and the irrigation fluid outlet opening or the fluid lines behind them close automatically when the first connecting means or the second connecting means is pulled off or separated. As a result, the passage is closed when no further irrigation fluid needs to be guided through the knee spacer system.

Particularly variable knee spacer systems can be characterized in that the irrigation liquid inlet opening is a first irrigation liquid inlet opening, and the irrigation liquid outlet opening is a first irrigation liquid outlet opening, wherein additionally, a second irrigation liquid inlet opening and a second irrigation liquid outlet opening are provided in the surface of the tibia prosthetic body, wherein at each of the first irrigation liquid inlet opening, the second irrigation liquid inlet opening, the first irrigation liquid outlet opening and the second irrigation liquid outlet opening, one self-sealing coupling is arranged, wherein the first connecting means is connectable in a fluid-tight and detachable manner with the first irrigation liquid inlet opening and with the second irrigation liquid inlet opening, and the second connecting means is connectable in a fluid-tight and detachable manner with the first irrigation liquid outlet opening and with the second irrigation liquid outlet opening, wherein the first irrigation liquid inlet opening and the second irrigation liquid inlet opening are connected in a fluid-permeable manner with each other in the tibia prosthetic body, and the first irrigation liquid outlet opening and the second irrigation liquid outlet opening are connected in a fluid-permeable manner with each other in the tibia prosthetic body.

As a result of these measures, the access to the knee spacer system can be variably selected and individually adapted to each situation and the specific patient. The self-sealing coupling closes automatically when no connecting means (the first or second connecting means) is connected or a connecting means is removed and opens when a connecting means is connected, and remains open for as long as the connecting means is connected.

With knee spacer systems with multiple irrigation fluid inlet openings and irrigation fluid outlet openings, it can be provided that the first irrigation liquid inlet opening and the first irrigation liquid outlet opening is arranged on a first side of the tibia component in relation to the sagittal plane, and the second irrigation liquid inlet opening and the second irrigation liquid outlet opening is arranged on a second side of the tibia component in relation to the sagittal plane, wherein in a particularly preferred manner, the first irrigation liquid inlet opening and the first irrigation liquid outlet opening are arranged in relation to the sagittal plane in a mirror-inverted manner to the second irrigation liquid inlet opening and to the second irrigation liquid outlet opening in the surface of the tibia prosthetic body. As a result, the connections can be allocated in an anatomically particularly advantageous manner.

It can also be provided that the cross-sectional area of the at least one irrigation liquid entry opening is at least just as large as the cross-sectional area of the irrigation liquid inlet opening and/or the total of the cross-sectional areas of the at least one irrigation liquid exit opening is at least just as large as the cross-sectional area of the irrigation liquid outlet opening.

As a result, stagnation point pressure in the interior of the tibia prosthetic body can be avoided.

Additionally, it can be provided that the at least one irrigation liquid exit opening and the at least one irrigation liquid entry opening are separated from the at least one mounting surface by a surrounding ridge that rises from the surface of the prosthetic body.

When the knee spacer system is used correctly, it can be prevented that the first and second connecting means and the irrigation fluid inlet opening and the irrigation fluid outlet opening are covered with bone cement and as a result, their functioning is impaired. In particular, it can be prevented that the hardened bone cement prevents a pulling off or a loosening of the first and second connecting means from the tibia prosthetic body.

It can further be provided that at least one irrigation fluid exit opening of the at least one irrigation fluid exit opening and/or at least one irrigation fluid entry opening of the least one irrigation fluid entry opening is or are arranged between the running surfaces.

As a result, it is achieved that the medical irrigation fluid exits between the running surfaces and very close to a femur component that forms the counterpiece to the tibia component, in particular, it exits between the running surfaces and very close to condyles of the femur component, and as a result, the irrigation fluid is distributed with a movement of the knee between the tibia component and the femur component. As a result, the joint can be well irrigated with the medical irrigation fluid with a movement of the knee spacer system.

According to a further development, it can be provided that the at least one irrigation fluid exit opening and the at least one irrigation fluid entry opening are arranged outside the running surfaces, wherein preferably, one irrigation fluid exit opening of the at least one irrigation fluid exit opening and one irrigation fluid entry opening of the least one irrigation fluid entry opening are arranged adjacent to one of the running surfaces, preferably within 3 mm adjacent to one of the running surfaces.

As a result, it is ensured that the at least one irrigation fluid exit opening and the at least one irrigation fluid entry opening do not impair the functioning of the running surfaces. Additionally, in this way, a mechanical stress and the resulting unwanted wear of the edges of the at least one irrigation fluid exit opening and the at least one irrigation fluid entry opening can be prevented.

In order to control the irrigation fluid circuit, it can be provided that in the first connecting means or in the irrigation fluid inlet opening, a first valve element is arranged that prevents a return flow of the irrigation fluid into the first connecting means, and/or in the second connecting means or in the irrigation fluid outlet opening, a second valve element is arranged that prevents a return flow of the irrigation fluid into the second connecting means, wherein preferably, the first and second valve element are selected from a non-return valve, a ball valve with spring, a lip valve, a Bunsen valve or a plate valve.

As a result, a circulating circuit of medical irrigation fluid can be enforced. Additionally, in this way, a return flow of the used medical irrigation fluid and thus a contamination of the irrigation fluid source or lines in the tibia prosthetic body can be prevented.

Additionally, for this purpose, it can be provided that in a first line within the tibia prosthetic body, which connects the at least one irrigation fluid entry opening with the irrigation fluid outlet opening in a fluid-permeable manner, a first valve is arranged which can only be opened by applying negative pressure to the irrigation fluid outlet opening, and which prevents a return flow of the irrigation fluid into the first line, and/or in a second line within the tibia prosthetic body, which connects the at least one irrigation fluid exit opening with the irrigation fluid inlet opening in a fluid-permeable manner, a second valve is arranged which can only be opened by applying negative pressure to the irrigation fluid inlet opening, and which prevents a return flow of the irrigation fluid into the second line.

As a result of this, too, a return flow of the used medical irrigation fluid can be prevented. Additionally, it can thus be ensured that without the connecting means, an exchange occurs between the irrigation fluid contained and surrounding fluids.

Further, it can be provided that in the tibia prosthetic body, the irrigation fluid inlet opening, the irrigation fluid outlet opening, the at least one irrigation fluid exit opening and the at least one irrigation fluid entry opening and the fluid-permeable connections are formed, wherein the tibia prosthetic body is preferably made of plastic, metal, ceramic, glass ceramic, bone cement or a combination of these.

As a result, a compact structure is achieved and the tibia prosthetic body takes the external appearance of a standard tibia component, with the exception of the openings.

For better accessibility of the connections, it can be provided that the irrigation fluid inlet opening and the irrigation fluid outlet opening are arranged in a side surface of the tibia prosthetic body or on a lateral side surface of the tibia prosthetic body.

As a result, a feed and discharge of the irrigation fluid into and out of the knee spacer system can be arranged in an anatomically easy and convenient manner. On the lateral side surface, the connecting means connected at the irrigation fluid inlet opening and the irrigation fluid outlet opening interfere to a particularly low degree.

With the invention, it is also recommended that at least one first irrigation fluid exit opening of the at least one irrigation fluid exit opening is arranged on the proximal side in the surface of the tibia prosthetic body, and at least one second irrigation fluid exit opening of the at least one irrigation fluid exit opening is arranged on the distal side in the surface of the tibia prosthetic body, and at least one first irrigation fluid entry opening of the at least one irrigation fluid entry opening is arranged on the proximal side in the surface of the tibia prosthetic body, and at least one second irrigation fluid entry opening of the at least one irrigation fluid entry opening is arranged on the distal side in the surface of the tibia prosthetic body.

It can hereby be ensured that both sides of the tibia prosthetic body can be irrigated with the medical irrigation fluid.

With preferred knee spacer systems, it can also be provided that the knee spacer system has a femur component, wherein the femur component has two condyles on one distal side As a result, the knee spacer system is completed and a femur component that matches the tibia component is provided, the condyles of which can slide such that they fit on the running surfaces of the tibia component.

It can here by provided that the condyles of the femur component are suitable for rolling on the running surfaces of the tibia component. The fact that the condyles of the femur component can run on the running surfaces of the tibia component means that the femur component and the tibia component can move against each other like a knee joint. The knee spacer or knee spacer system is an articulating prosthesis designed to replace a knee joint, including its function.

Preferably, the femur component has multiple bound mounting surfaces on the proximal side, which are bound with a surrounding ridge that rises from the proximal surface of the femur component, or which are separated from each other by the ridge that rises from the proximal surface. Within these holders for the bone cement paste that are bound by ridges of the femur component, the femur component is attached to the femur. Between the mounting surfaces, the medical irrigation fluid can then flow, so that the distal surface of the femur can also be reached by the irrigation fluid. Additionally, the ridges can be used to set the thickness of the desired adhesive gap.

Preferably, it can also be provided that the femur component has a femur prosthetic body, wherein the femur prosthetic body has at least one mounting surface for mounting the femur component with a bone cement to a femur on one proximal side of the femur prosthetic body, the femur component further having a third tubular and fluid-permeable connecting means for feeding a medical irrigation fluid into the femur prosthetic body, a fourth tubular and fluid-permeable connecting means for draining a medical irrigation fluid from the femur prosthetic body, an irrigation fluid inlet opening in a surface of the femur prosthetic body, wherein the third connecting means is connected or connectable in a fluid-permeable manner to the irrigation fluid inlet opening of the femur prosthetic body, an irrigation fluid outlet opening in a surface of the femur prosthetic body, wherein the fourth connecting means is connected or connectable in a fluid-permeable manner to the irrigation fluid outlet opening of the femur prosthetic body, at least one irrigation fluid exit opening in the surface of the femur prosthetic body, which is connected in the interior of the femur prosthetic body with the irrigation fluid inlet opening of the femur prosthetic body in a fluid-permeable manner, and at least one irrigation fluid entry opening in the surface of the femur prosthetic body, which is connected in the interior of the femur prosthetic body with the irrigation fluid outlet opening of the femur prosthetic body in a fluid-permeable manner, wherein the at least one irrigation fluid exit opening of the femur prosthetic body and the at least one irrigation fluid entry opening of the femur prosthetic body are arranged outside the at least one mounting surface of the femur prosthetic body.

As a result, an irrigation with the medical irrigation fluid can also be achieved in the area of the femur. A connection of the irrigation fluid circuits is not provided, but is possible in principle. For example, the second connecting means could be used as the third connecting means, or the second connecting means could be designed as a single part with the third connecting means, and thus the irrigation fluid could be fed from the tibia component into the femur component. Preferably, the irrigation fluid circuits of the tibia component and the femur component are however kept separate from each other for hygiene reasons, and thus no mutual infection can occur.

With such knee spacer systems, it can be provided that the at least one irrigation fluid exit opening of the femur prosthetic body and the at least one irrigation fluid entry opening of the femur prosthetic body are arranged outside the condyles of the femur prosthetic body.

It is hereby ensured that the at least one irrigation fluid exit opening and the at least one irrigation fluid entry opening of the femur prosthetic body do not impair the functioning of the condyles. Additionally, in this way, a mechanical stress and the resulting unwanted wear of the edges of the at least one irrigation fluid exit opening of the femur prosthetic body and the at least one irrigation fluid entry opening of the femur prosthetic body in the area of the condyles can be prevented.

Finally, it can be provided that at least one irrigation fluid exit opening of the at least one irrigation fluid exit opening or at least one irrigation fluid entry opening of the least one irrigation fluid entry opening is arranged on a distal side of a protrusion extending in the distal direction between two mounting surfaces of the tibia component.

It is hereby achieved that the irrigation fluid can also reach the mounting surface in the tibia.

SUMMARY OF THE DRAWINGS

Further exemplary embodiments of the invention will be described below with reference to fifteen schematic figures, without thereby restricting the invention. In the drawings.

DETAILED DESCRIPTION

Figure 1:
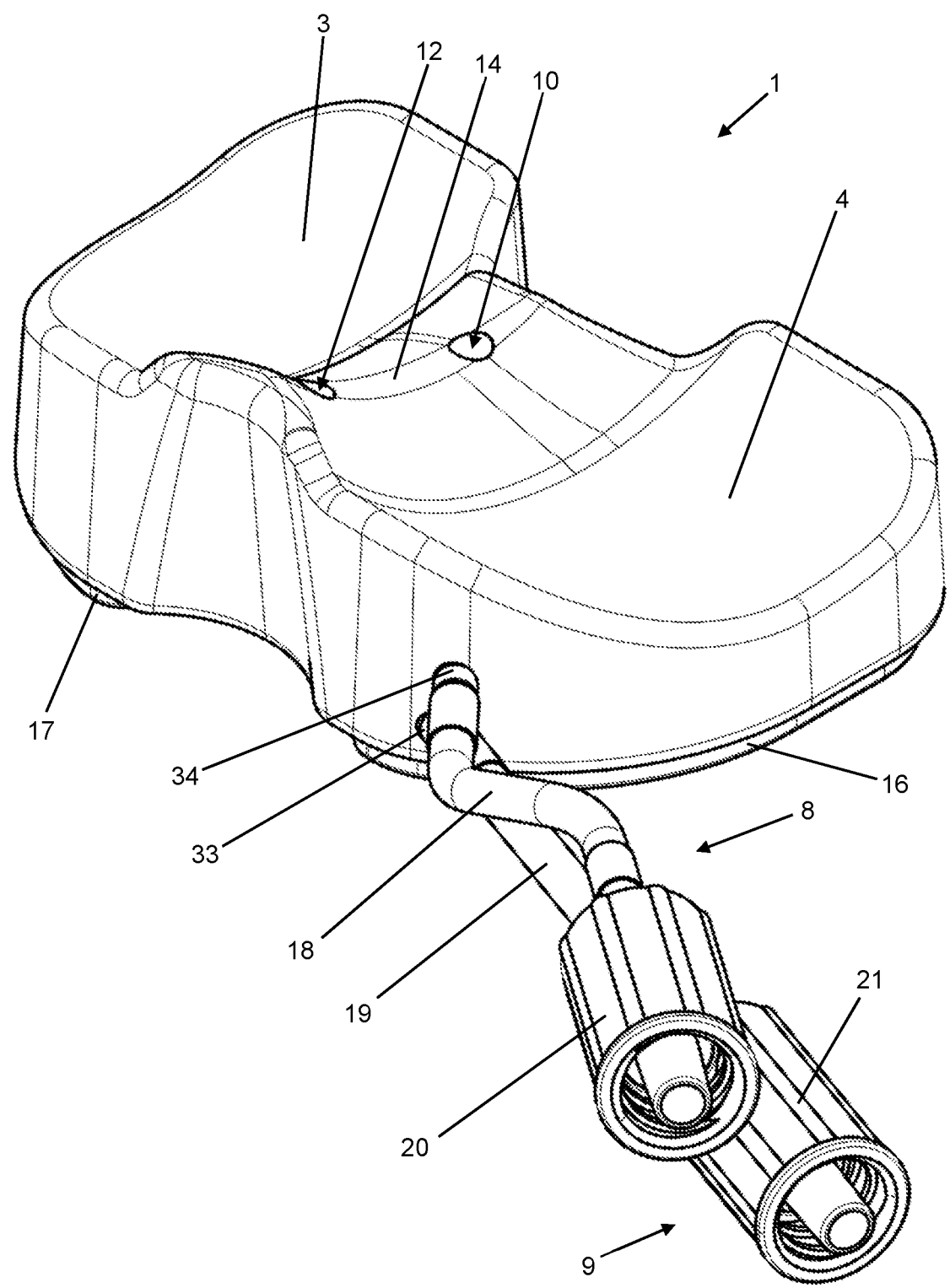
FIG. 1: shows a schematic perspective view onto the proximal side of a tibia component as the first knee spacer system according to the invention.
Figure 2:
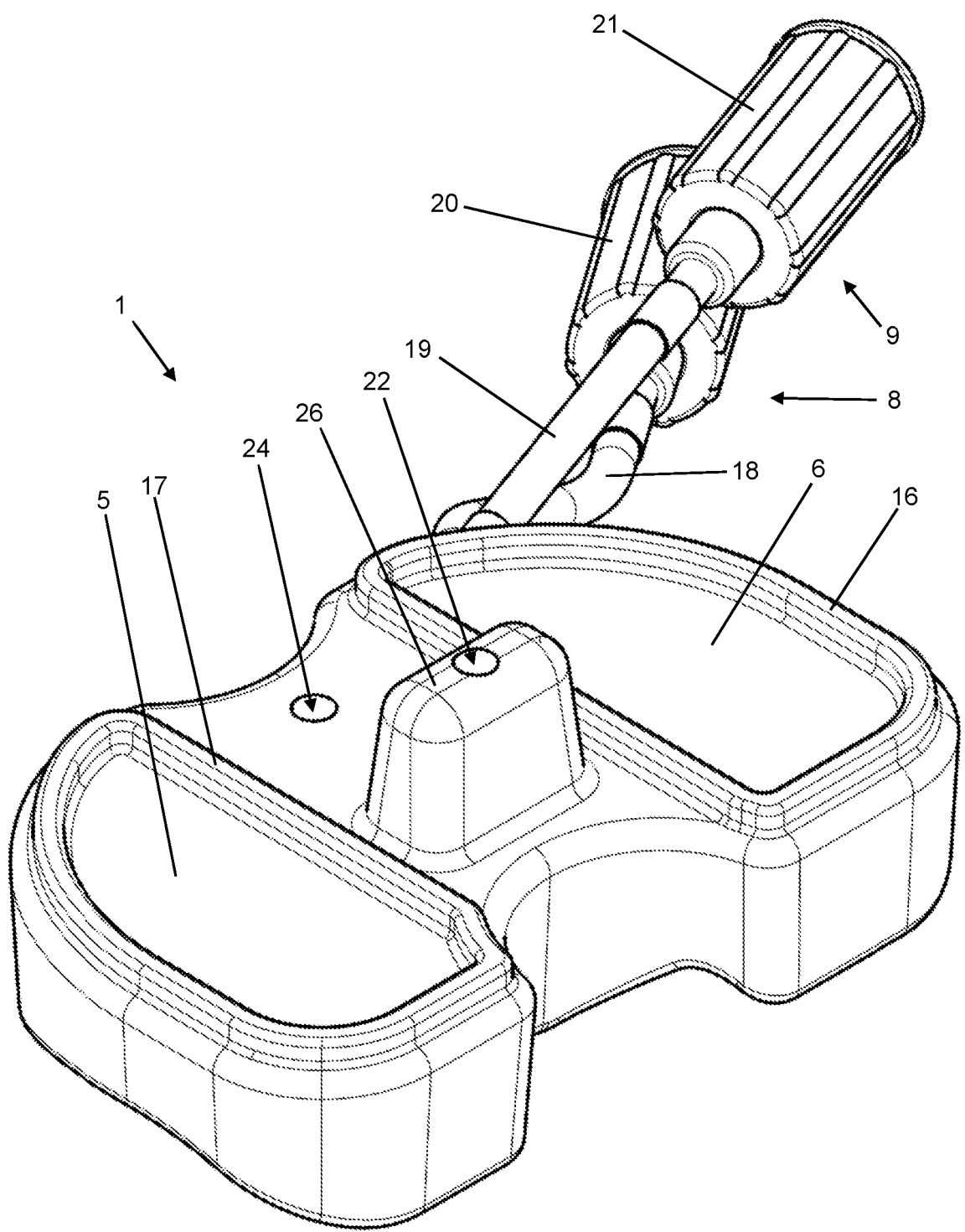
FIG. 2: shows a schematic perspective view onto the distal side of the tibia component according to FIG. 1.
Figure 3:
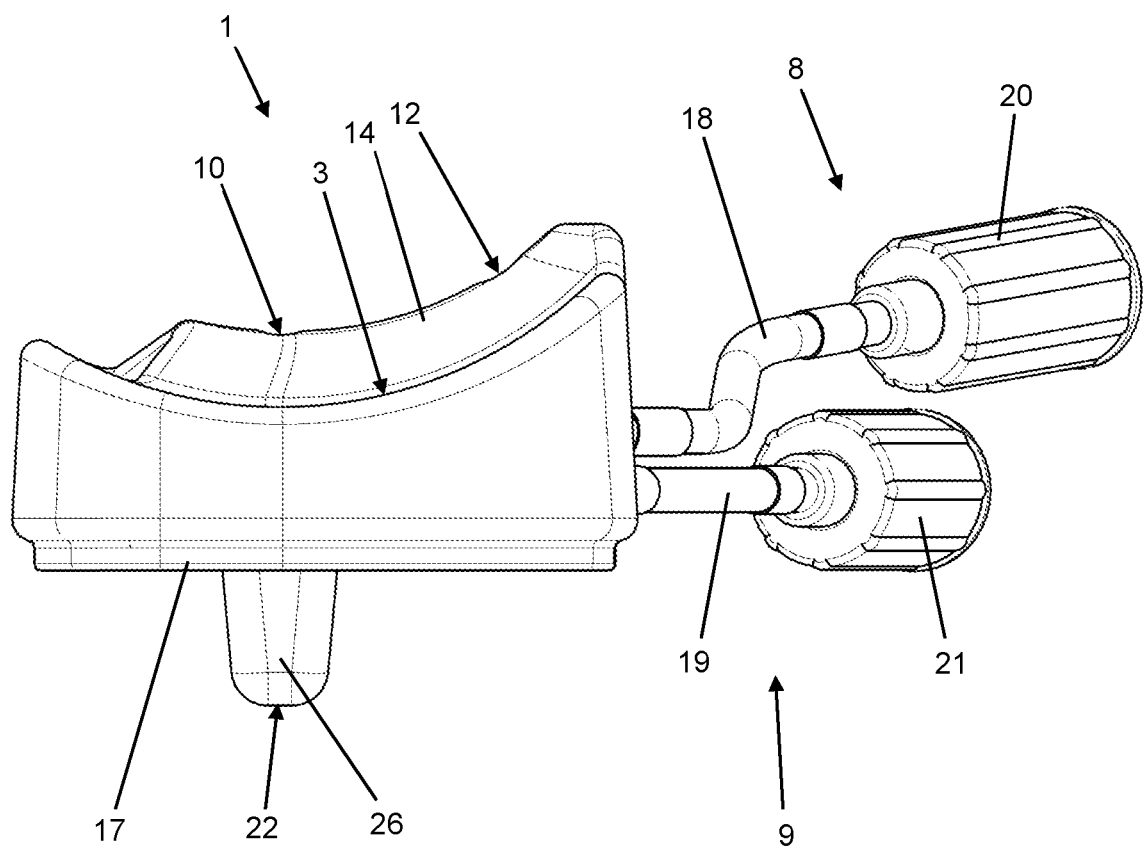
FIG. 3: shows a schematic side view onto a lateral side of the tibia component according to FIGS. 1 and 2.

The invention is based on the surprising finding that a temporary knee spacer system with a tibia component can be used for the continuous irrigation of a cavity in the body of a patient, whereby on the surface of the tibia prosthetic body of the knee spacer system, suitable openings are provided, and suitable lines are provided for the irrigation fluid in the interior of the tibia prosthetic body, and whereby two connection means that are accessible from the outside are connected or connectable, through which the medical irrigation fluid can be fed into the tibia prosthetic body and the used irrigation fluid can again be discharged from the tibia prosthetic body. With the knee spacer system, both a distal and a proximal side of a tibia component can hereby be irrigated via separate circuits of the irrigation fluid, so that the plateau on which the tibia is placed does not need to be irrigated by the irrigation fluid.

The knee spacer system according to the invention can advantageously be used as part of two-stage septic revisions, in which an infection with two or more microbial germs and in particular with problematic germs has occurred. It is particularly advantageous that the spacer components and the surrounding soft tissue and at least partially also surrounding bone tissue can be irrigated with antibiotic solutions, such as antibiotics and also antiseptics, or in special cases with antimycotics, whereby the type and number of active substances and above all the concentration of the antimicrobial active substances in the irrigation fluid can be precisely adjusted. Through suctioning off of the irrigation fluid, the dwell time of the antimicrobial irrigation fluid in the patient can be precisely adjusted. As a result, it is possible for the first time to guarantee over several days an irrigation of the surfaces of the knee spacer system with precisely pre-adjusted concentrations of antimicrobial active substances in the irrigation fluid. As a result, the protection against microbial re-infection of the surfaces of the knee spacer system is significantly reduced compared to the spacers produced from bone cement used to date. After antibiotic irrigation, it is possible to rinse the surfaces of the knee spacer system and the surrounding tissue with an active substance-free irrigation fluid. As a result, residues of the antimicrobial active substances are removed. Resistance formation as a result of persisting active substance residues is therefore extremely unlikely.

Further, it is advantageous that the irrigation fluids can also contain such antimicrobial active substances that normally cannot be integrated into the spacers made of bone cement, since these would hinder or prevent radical polymerization. Examples of these are the active substances Rifampicin and Metronidazol.

If it can be seen from the clinical parameters that the infection or inflammation is declining, the connecting means can be removed from the tibia component. For this purpose, the connecting means is advantageously connected with an outer thread or via a bayonet connection or via a plug-in connection with the at least one irrigation fluid inlet opening and the at least one irrigation fluid outlet opening. Preferably, the at least one irrigation fluid inlet opening and the at least one irrigation fluid outlet opening are arranged close next to each other or over each other at the side in the tibia component next to the duct of the patella or the patella fascia.

Preferably, it can be provided that the at least one irrigation fluid inlet opening and the at least one irrigation fluid outlet opening close flush with the surface of the tibia prosthetic body after removal of the connecting means, in order to prevent an irritation of the surrounding soft tissue.

An exemplary knee spacer according to the invention can be compiled of

A) a tibia component with two running surfaces on the proximal side
B) an irrigation fluid inlet opening arranged on the surface of the tibia component
C) a tubular, fluid-permeable first connecting means for feeding in the irrigation fluid, which is detachably connected to the irrigation fluid inlet opening
D) at least one irrigation fluid outlet opening on the surface of the tibia component, which is connected in a fluid-permeable manner via a first line in the interior of the tibia component with the irrigation fluid inlet opening
E) at least one irrigation fluid inlet opening on the surface of the tibia component
F) at least one irrigation fluid outlet opening on the surface of the tibia component
G) a fluid-permeable, tubular second line in the interior of the tibia component, which connects the irrigation fluid inlet opening with the irrigation fluid outlet opening in a fluid-permeable manner
H) a tubular, fluid-permeable second connecting means for suctioning off the irrigation fluid, which is detachably connected to the irrigation fluid outlet opening
I) at least one mounting surface enclosed by a ridge for holding bone cement on the surface of the distal side of the tibia component, and
J) a femur component that has two condyles, which correspond to the running surfaces of the tibia component.

Preferably, the profile of the irrigation fluid entry opening is larger or equal to the profile of the irrigation fluid inlet opening.

It can be provided according to the invention that at least one irrigation fluid exit opening is arranged on the proximal side and at least one irrigation fluid exit opening is arranged on the distal side of the tibia component. Due to the irrigation fluid outlet opening arranged on the proximal side, the running surfaces of the tibia component, the lateral parts of the tibia component and the parts of the femur component that are accessible for the irrigation fluid can be irrigated. Due to the irrigation fluid exit opening arranged on the distal side, the bone tissue can at least partially be irrigated on the distal side of the tibia component. As a result, it is also possible to rinse the proximal marrow space of the tibia when the irrigation fluid exit opening arranged on the distal side of the tibia component is arranged approximately centrally.

It is also advantageous when at least one irrigation fluid entry opening is arranged on the proximal side and at least one irrigation fluid entry opening is arranged on the distal side of the tibia component. As a result, unhindered suctioning off of the irrigation fluid in both areas is possible.

The space between the irrigation fluid exit opening and the irrigation fluid entry opening is at least 0.5 cm, preferably at least 2.0 cm and very particularly preferred, at least 3.0 cm. As a result, it is guaranteed that the irrigation fluid can take up sufficient debris and wound secretion before being suctioned off again through the irrigation fluid entry opening via the line.

It can advantageously also be provided that the at least one irrigation fluid exit opening and the at least one irrigation fluid entry opening are arranged on the proximal side of the tibia component next to the running surfaces. As a result, the sliding behavior of the tibia component against the femur component is not impaired. Openings in the running surfaces can facilitate the formation of wear particles with sliding pairs, and are therefore disadvantageous or must be suitably designed, which involved effort.

According to the invention, it can also be provided that at least one irrigation fluid exit opening and at least one irrigation fluid entry opening are arranged on the proximal and on the distal side of the tibia component, whereby the total of the profiles of the irrigation fluid entry openings is greater or equal to the profile of the irrigation fluid exit openings. As a result, it is guaranteed that no congestion effects occur when the irrigation fluid is being suctioned off.

It can also be provided according to the invention that between the irrigation fluid inlet opening and the first connecting means, a return valve is arranged that prevents a return flow of the irrigation fluid into the first connecting means, whereby a ball valve with spring, a lip valve, a Bunsen valve and a plate valve are preferred as a return valve.

According to the invention, it can also be provided that between the irrigation fluid outlet opening and the second connecting means, a return valve is arranged that prevents a return flow of the irrigation fluid into the second connecting means, whereby a ball valve with spring, a lip valve, a Bunsen valve and a plate valve are preferred as a return valve.

Further, it can be provided according to the invention that between the at least one irrigation fluid outlet opening and the connected line in the tibia prosthetic body, a valve is arranged that can only be opened by applying a negative pressure to the line, so that a return flow of the used irrigation fluid into the line is prevented, whereby a ball valve with spring, a lip valve, a Bunsen valve and a plate valve are preferred as a return valve.

Equally, it can be provided according to the invention that between the at least one irrigation fluid entry opening and the connected line in the tibia prosthetic body, a valve is arranged that can only be opened by applying a negative pressure to the line, so that a return flow of the used irrigation fluid into the line is prevented, whereby a ball valve with spring, a lip valve, a Bunsen valve and a plate valve are preferred as a return valve.

It can advantageously also be provided that on the surface of the distal side of the femur component, two or more areas bound by ridges are arranged for holding bone cement. As a result, the irrigation fluid can have an effect on the bone tissue on the distal femur which is not covered by bone cement.

The knee spacer system according to the invention can be made from plastic, metal, ceramic, glass ceramic and combinations of these. Advantageously, the knee spacer system can also consist of hardened bone cement. The bone cement can additionally contain antimicrobial active substances, such as antiseptics, antibiotics and antimycotics.

FIGS. 1 to 6 show images of a tibia component 1 as the first knee spacer system according to the invention with an irrigation device. FIG. 7 shows a corresponding femur component 2, which together with the tibia component 1 according to FIGS. 1 to 6 can form a knee spacer system according to the invention for a complete knee joint.

The tibia component 1 comprises on its proximal side two running surfaces 3, 4 (see, in particular, FIG. 1). The running surfaces 3, 4 form a roll-off surface of the knee joint or knee spacer system. On the opposite, distal side of the tibia component 1, two mounting surfaces 5, 6 are arranged (see in particular FIG. 2), which are provided for the connection of the tibia component 1 with a tibia (not shown) with the aid of bone cement paste. The running surfaces 3, 4 and the mounting surfaces 5, 6 are arranged on a tibia prosthetic body, the outer form of which essentially corresponds to the outer form of a tibia component of a standard knee spacer.

On a side surface of the tibia prosthetic body, in contrast to the tibia components of known knee spacer systems, a first, tubular connecting means 8 for feeding an irrigation fluid to an irrigation fluid inlet opening is affixed, and a second tubular connecting means 9 is connected for discharging an irrigation fluid on an irrigation fluid outlet opening. The irrigation fluid inlet opening and the irrigation fluid outlet opening are arranged in the tibia prosthetic body and lead into the interior of the tibia prosthetic body. The first tubular connecting means 8 and the second tubular connecting means 9 are fluid-permeable, so that a medical irrigation fluid can be guided into the tibia prosthetic body through the first tubular connecting means 8, and a fluid can be discharged through the second tubular connecting means 9 from the tibia prosthetic body. The first connecting means 8 and the second connecting means 9 are detachably connected to the irrigation fluid inlet opening and the irrigation fluid outlet opening.

On the proximal surface of the tibia component 1, an irrigation fluid exit opening 10 and an irrigation fluid entry opening 12 are arranged on a bridge 14 between the running surfaces 3, 4. The mounting surfaces 5,6 are in each case bound by one circumferential ridge 16, 17 each. The ridges 16, 17 rise from the distal surface of the tibia component 1 and are to be regarded as a part of the tibia prosthetic body.

The first connecting means 8 has a short, flexible hose 18 and Luer lock adapter 20. Equally, the second connecting means 9 has a short, flexible hose 19 and Luer lock adapter 21. As a result, the tibia component 1 with the first connecting means 8 can be conveniently connected via the Luer lock adapter 20 to a source for a medical irrigation fluid with a pump (not shown), and the second connecting means 9 can also be connected via the Luer lock adapter 21 to a collecting tray and if necessary also a pump (not shown).

Due to the protruding ridges 16, 17 around the mounting surfaces 5, 6, it is prevented or at least hindered that when the tibia component 1 is being attached on the tibia, bone cement exits out of the mounting surfaces 5, 6 and as a result, the proximal irrigation fluid exit opening 10, the proximal irrigation fluid entry opening 12, the distal irrigation fluid exit opening 22, the distal irrigation fluid entry opening 24 or the irrigation fluid inlet opening and the irrigation fluid outlet opening closes or impairs or unintentionally firmly cements the first connecting means 8 or the second connecting means 9 on the tibia prosthetic body.

On the distal surface of the tibia component 1, an irrigation fluid exit opening 22 and an irrigation fluid entry opening 24 are arranged between the running surfaces 5, 6. The distal irrigation fluid exit opening 22 is arranged on a distal protrusion 26. The distal protrusion 26 is provided for anchoring the tibia component 1 or the tibia prosthetic body in the tibia.

Figure 4:
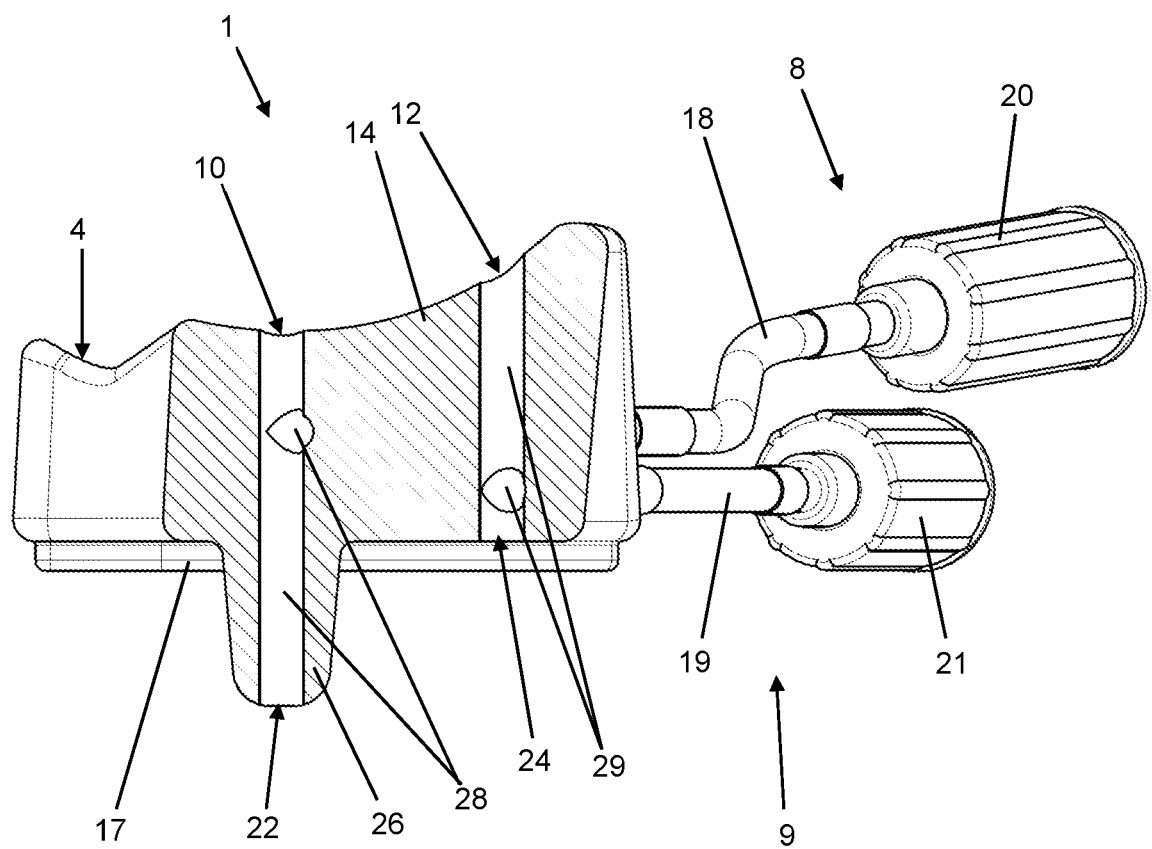
FIG. 4: shows a side profile view of the tibia component along a sagittal plane of the tibia component according to FIGS. 1 to 3.
Figure 5:
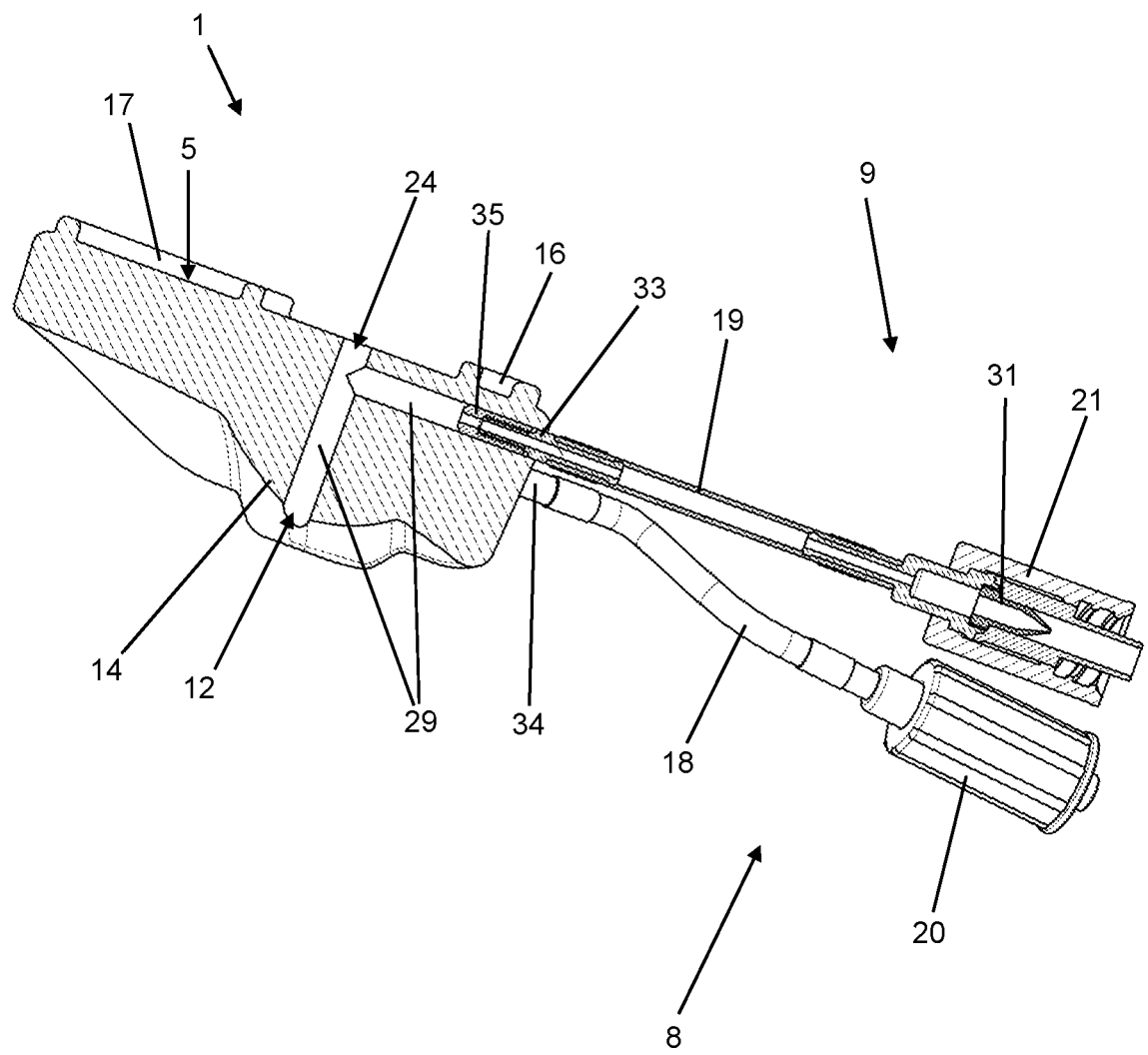
FIG. 5: shows a second side profile view of the tibia component according to FIGS. 1 to 4.
Figure 6:
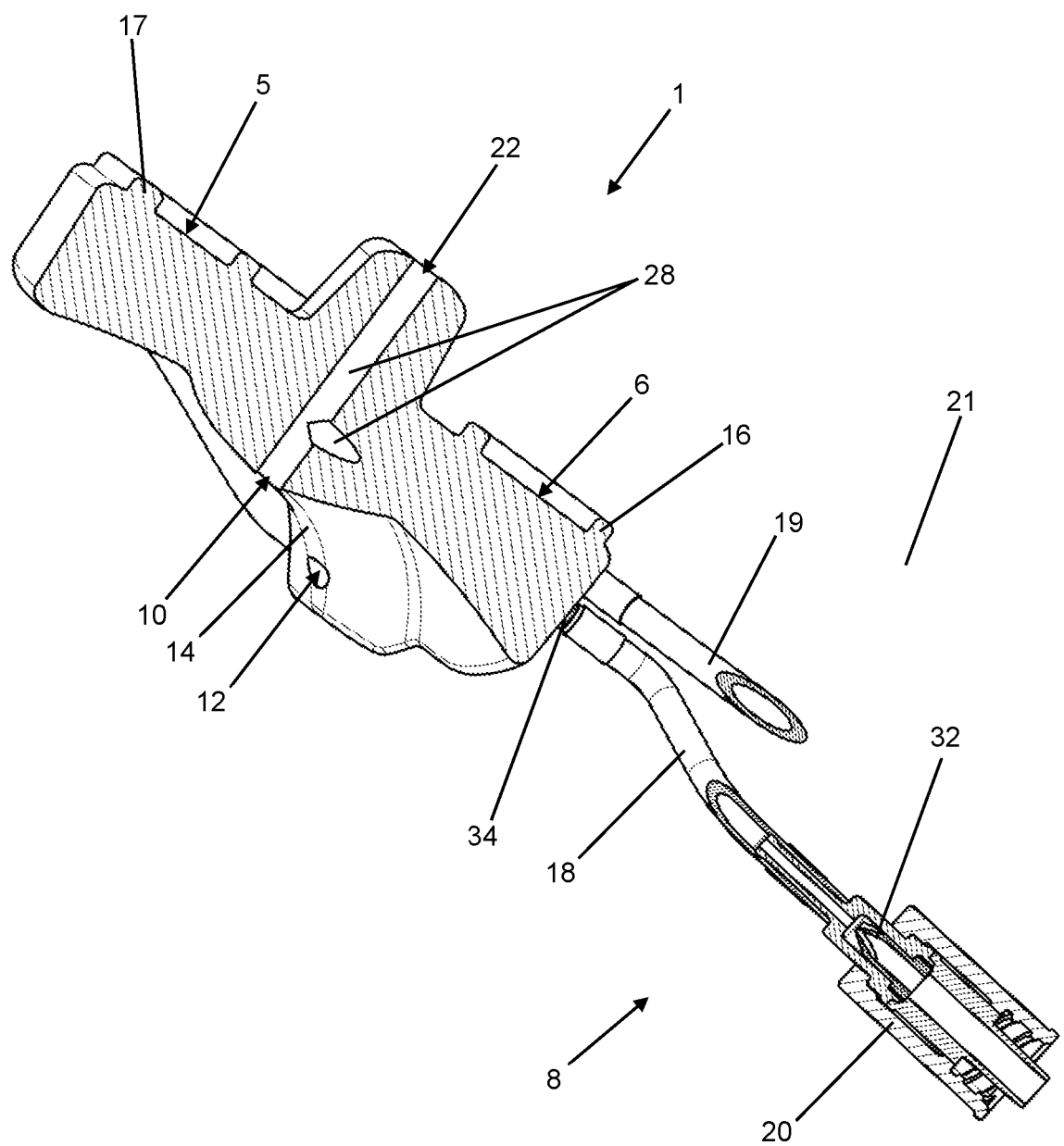
FIG. 6: shows a third side profile view of the tibia component according to FIGS. 1 to 5.
Figure 7:
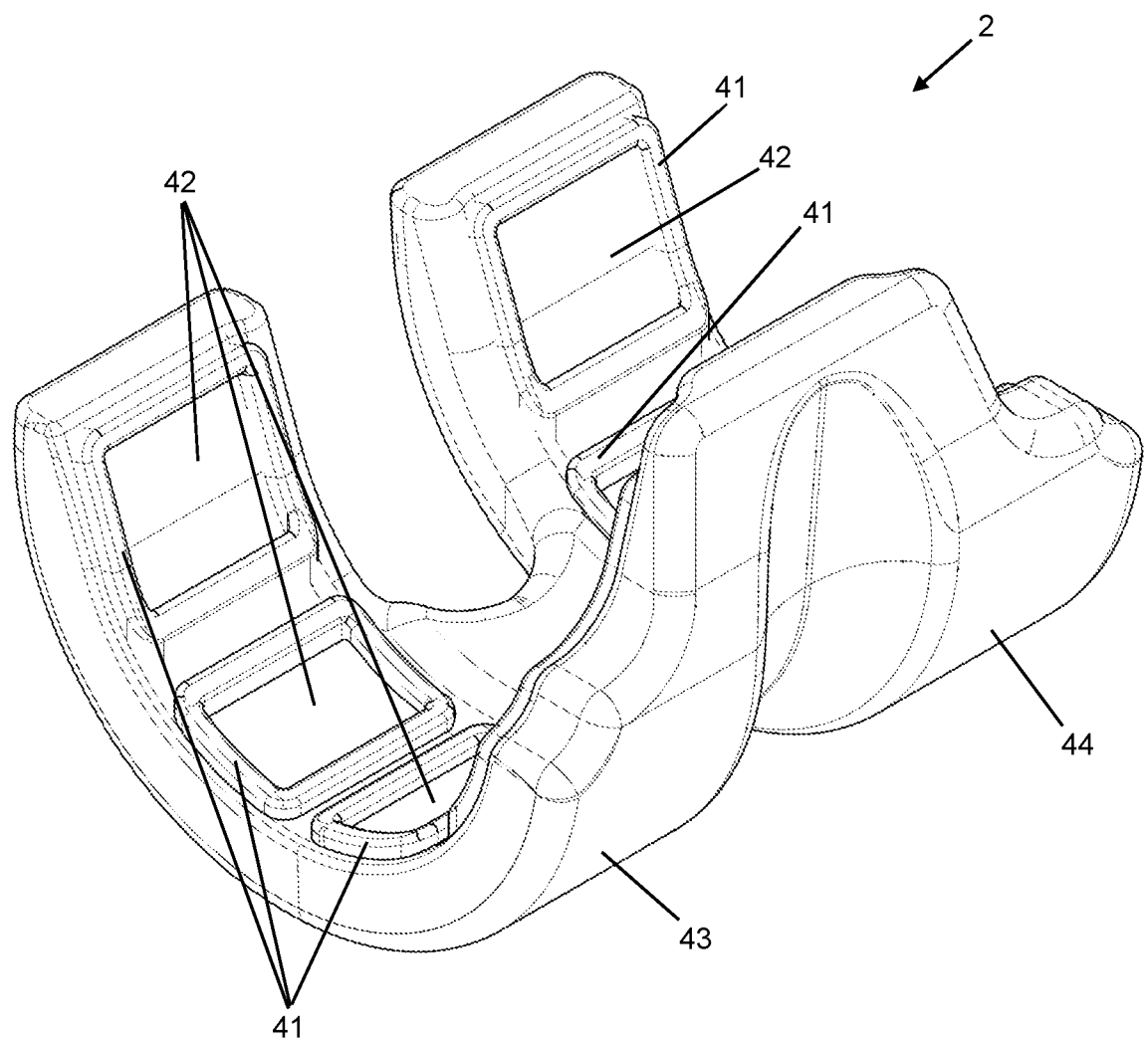
FIG. 7: shows a schematic perspective view onto the proximal side of an exemplary femur component for a knee spacer system according to the invention.

In the profile views shown in FIGS. 4, 5 and 6, it can largely be seen how the irrigation fluid outlet opening with the proximal irrigation fluid entry opening 12 and the distal irrigation fluid entry opening 24 and the irrigation fluid inlet opening are connected to the proximal irrigation fluid exit opening 10 and the distal irrigation fluid exit opening 22 in the interior of the tibia prosthetic body. The tibia prosthetic body is essentially made from plastic. Preferably from a bone cement, such as a PMMA plastic, which can be charged with an antibiotic or with several antibiotics and/or with at least one antimycotic.

In the interior of the tibia prosthetic body, the irrigation fluid inlet opening is connected to the proximal irrigation fluid exit opening 10 and the distal irrigation fluid exit opening 22 via a first line 28. The first line 28 creates a fluid-permeable connection between the irrigation fluid inlet opening and the proximal irrigation fluid exit opening 10 and the distal irrigation fluid exit opening 22. For this purpose, in the interior of the tibia prosthetic body, a branch in the form of a T-piece is provided in the first line 28 (see FIGS. 4 and 8). Equally, in the interior of the prosthetic body, the irrigation fluid outlet opening is connected to the proximal irrigation fluid entry opening 12 and the distal irrigation fluid entry opening 24 via a second line 29. The second line 29 also comprises a branch for this purpose in the form of a T-piece (see FIGS. 4 and 5). The first line 28 and the second line 29 are separated from each other in the interior of the tibia prosthetic body.

In the Luer lock adapter 21 of the second connecting means 9 for discharging the irrigation fluid, a valve element 31 is provided that permits an outflow of fluid from the second line 29 through the irrigation fluid outlet opening from the tibia prosthetic body and through the second connecting means 9, and which prevents a return flow from a drainage line connected on the Luer lock adapter 21 into the hose 19 of the second connecting means 9 into the second line 29. Equally, in the Luer lock adapter 20 of the first connecting means 8 for feeding an irrigation fluid, a second valve element 32 is provided that permits a feed of medical irrigation fluid through the first connecting means 8 and through the irrigation fluid inlet opening into the first line 28 and the tibia prosthetic body, and which prevents a return flow out of the hose 18 of the first connecting means 8 into a source of the medical irrigation fluid connected to the Luer lock adapter 20.

The second connecting means 9 is connected via a detachable connecting element 33 with the irrigation fluid outlet opening (see FIG. 5). In the same way, the first connecting means 8 is connected via a detachable connecting element 34 with the irrigation fluid inlet opening. The detachable connecting element 34 can only be seen in part from the outside (see FIG. 1). In order to connect the first connecting means 8 and the second connecting means 9 to the tibia prosthetic body, in the first line 28, a first counter-fastening element is arranged (not visible in the figures, but present), and in the second line 29, in the same manner, a second counter-fastening element 35 is arranged. The connecting elements 33, 34 can be attached or are attached to an inner thread of the two counter-fastening elements 35 via an outer thread. Alternatively, a bayonet connection or a plug-in connection can also be realized. The first connecting means 8 and the second connecting means 9 can thus be detached by the detachable connecting elements 33, 34 being pulled off or unscrewed from the tibia prosthetic body. The first counter-fastening element and the second counter-fastening element 35 are preferably designed such that they automatically close the irrigation fluid outlet opening and the irrigation fluid inlet opening when the connecting means 33, 34 are detached.

FIG. 7 shows a schematic perspective view onto the proximal side of the exemplary femur component 2, which together with the tibia component 1 is suitable for forming a knee spacer system according to the invention for replacing a complete knee joint. The femur component 2 has several mounting surfaces 42 on its proximal side, which are bound by ridges 41. The mounting surfaces 42 serve to connect the femur component 2 with the femur, whereby a bone cement connects the mounting surfaces 42 with the femur. The ridges 41 protrude in the proximal direction from the proximal surface of the femur component 2 and thus prevent an exit of bone cement between the mounting surfaces 42. As a result, the intermediate spaces between the mounting surfaces 42 remain free and can be irrigated by the irrigation fluid, so that the intermediate space between the femur component 2 and the femur is also reachable with the irrigation fluid.

On the distal side, the femur component 2 has two adjacent condyles 43, 44. The condyles 43, 44 can roll on the running surfaces of the tibia component 1, so that the femur component 2 and the tibia component 1 together form a knee spacer system according to the invention. Alternatively, however, another femur component together with the tibia component according to FIGS. 1 to 6 can be used to form a knee spacer system according to the invention, such as the femur component 52 shown in FIG. 8 or another already known femur component.

Figure 8:
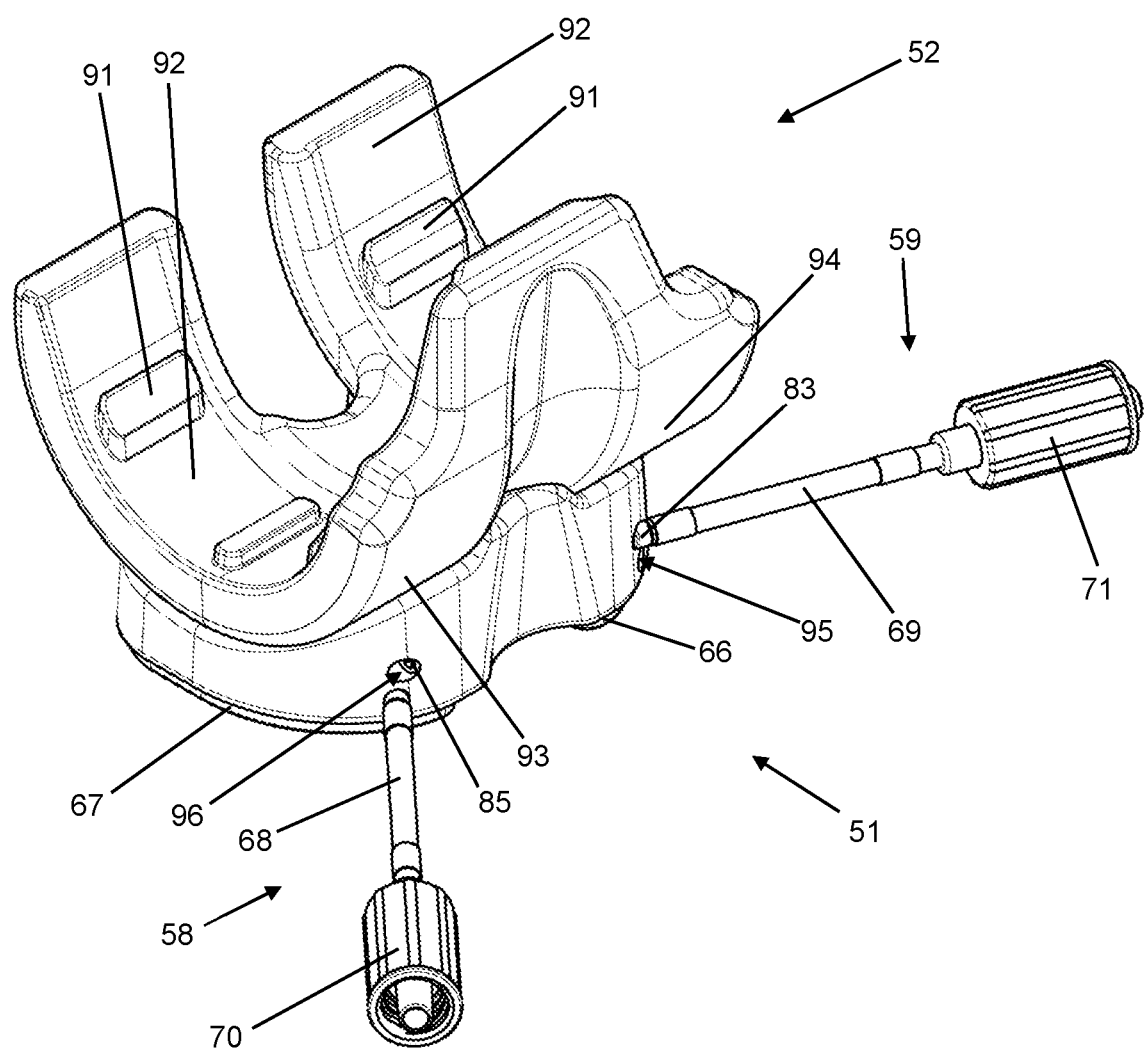
FIG. 8: shows a schematic perspective view onto the proximal side of an exemplary second knee spacer system according to the invention with a tibia component (below) and a femur component (above)
Figure 9:
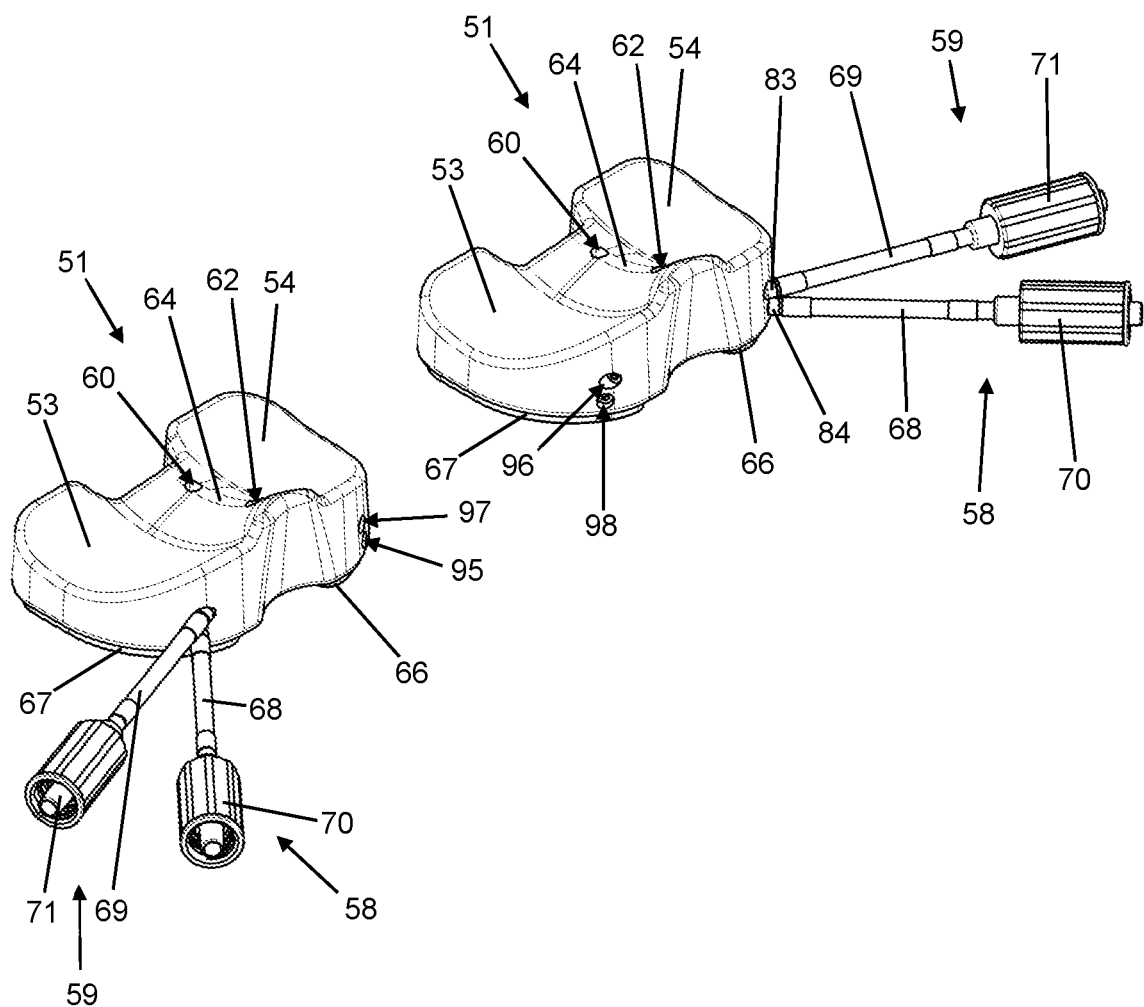
FIG. 9: shows two schematic perspective views onto the proximal side of the tibia component of the second knee spacer system according to the invention according to FIG. 8 with connections with different allocations.
Figure 10:
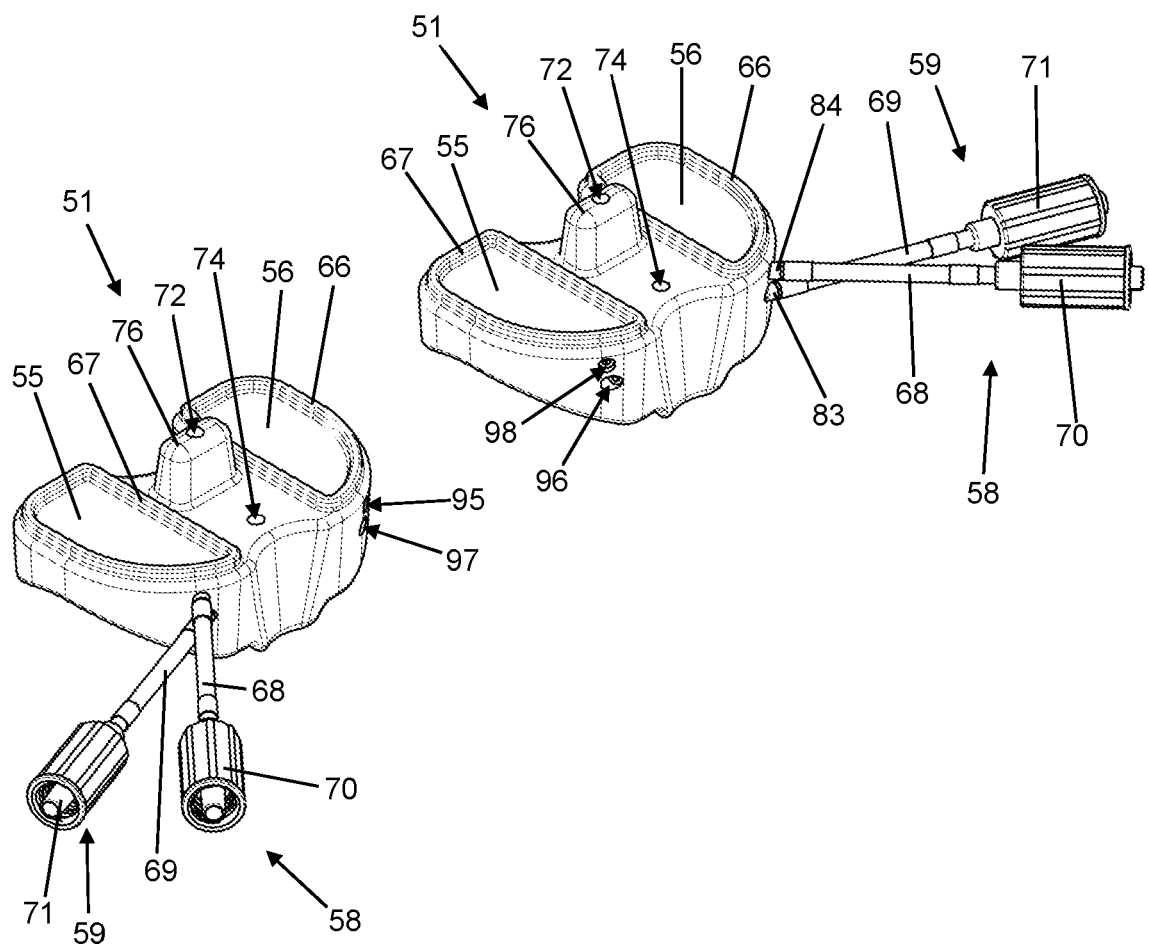
FIG. 10: shows two schematic perspective views onto the distal side of the tibia component according to FIG. 9.
Figure 11:
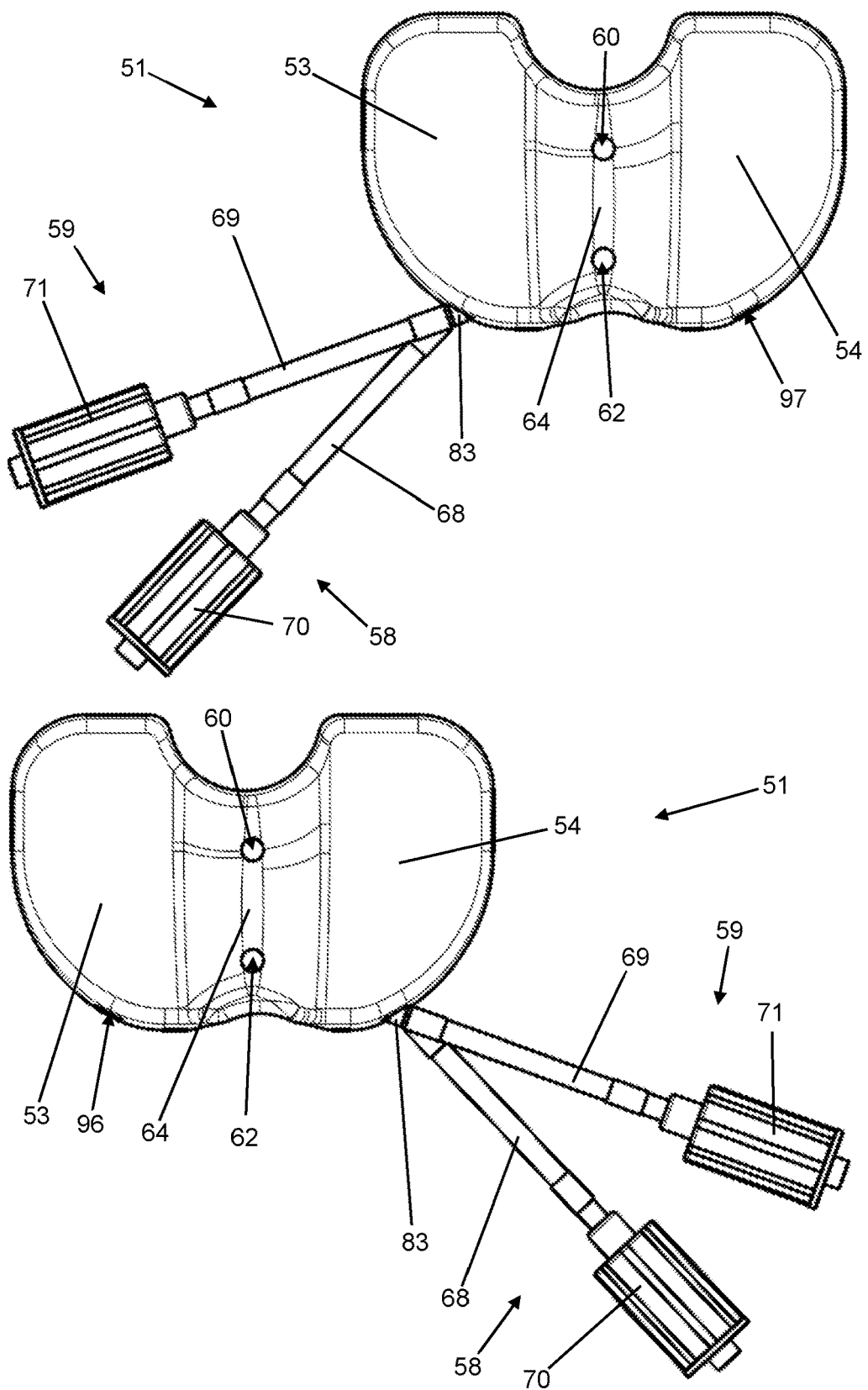
FIG. 11: shows two schematic side views onto the proximal side of the tibia component according to FIGS. 9 and 10.

FIGS. 8 to 15 show images of a tibia component 51 of a second alternative knee spacer system according to the invention with irrigation device. Here, FIG. 8 also shows a femur component 52 which together with the tibia component 51 forms the knee spacer system. FIG. 8 shows the tibia component 51 and the femur component 52 which lie correctly on each other, as the knee spacer system would also lie when inserted in the patient.

The tibia component 51 comprises on its proximal side two running surfaces 53, 54 (see FIGS. 9 and 11), on which the femur component 52 in FIG. 8 lies. The running surfaces 53, 54 form a roll-off surface of the knee joint or knee spacer system. On the opposite, distal side of the tibia component 51, two mounting surfaces 55, 56 are arranged (see in particular FIG. 10), which are provided for the connection of the tibia component 51 with the tibia with the aid of bone cement paste (not shown). The running surfaces 53, 54 and the mounting surfaces 55, 56 are arranged on a tibia prosthetic body, the outer form of which essentially corresponds to the outer form of a tibia component of a standard knee spacer.

On a side surface of the tibia prosthetic body, in contrast to the tibia components of known knee spacer systems, a first, tubular connecting means 58 for feeding an irrigation fluid to one of two irrigation fluid inlet openings 95, 98 is connected or connectable, and a second tubular connecting means 59 is connected for discharging an irrigation fluid on one of two irrigation fluid outlet openings 96, 97. The irrigation fluid inlet openings 95, 98 and the irrigation fluid outlet openings 96, 97 are arranged in the tibia prosthetic body and lead into the interior of the tibia prosthetic body. The paired arrangement in each case of two irrigation fluid inlet openings 95, 98 and irrigation fluid outlet openings 96, 97 enables a connection of the first connecting means 58 and the second connecting means 59 that is adapted to the individual situation. Additionally, in this manner, the tibia component 51 can easily be used both for the right and left knee, and at the same time, the connecting means 58, 59 can be guided laterally outwards, where they interfere to a lesser degree. The second embodiment mainly differs from the first embodiment shown in FIGS. 1 to 6 due to the larger number of openings 95, 96, 97, 98 and the resulting variability. The first tubular connecting means 58 and the second tubular connecting means 59 are fluid-permeable, so that a medical irrigation fluid can be guided into the tibia prosthetic body through the first tubular connecting means 58, and a fluid can be discharged through the second tubular connecting means 59 from the tibia prosthetic body. The first connecting means 58 and the second connecting means 59 are detachably and variably connected to one of the irrigation fluid inlet openings 95, 98 and one of the irrigation fluid outlet openings 96, 97.

On the proximal surface of the tibia component 51, an irrigation fluid exit opening 60 and an irrigation fluid entry opening 62 are arranged on a bridge 64 between the running surfaces 53, 54. The mounting surfaces 55, 56 are in each case bound by one circumferential ridge 66, 67 each. The ridges 66, 67 rise from the distal surface of the tibia component 51 and are to be regarded as a part of the tibia prosthetic body.

The first connecting means 58 has a short, flexible hose 68 and Luer lock adapter 70. Equally, the second connecting means 59 has a short, flexible hose 69 and Luer lock adapter 71. As a result, the tibia component 51 with the first connecting means 58 can be easily connected via the Luer lock adapter 70 to a source for a medical irrigation fluid with a pump (not shown), and the second connecting means 59 can also be connected via the Luer lock adapter 71 to a collecting tray and if necessary also a pump (not shown).

On the distal surface of the tibia component 51, an irrigation fluid exit opening 72 and an irrigation fluid entry opening 74 are arranged between the running surfaces 55, 56. The distal irrigation fluid exit opening 72 is arranged on a distal protrusion 76. The distal protrusion 76 is provided for anchoring the tibia component 51 or the tibia prosthetic body in the tibia.

Due to the protruding ridges 66, 67 around the mounting surfaces 55, 56, it is prevented or at least hindered, that when the tibia component 51 is being attached on the tibia, bone cement exits out of the mounting surfaces 55, 56 and as a result, the proximal irrigation fluid exit opening 60, the proximal irrigation fluid entry opening 62, the distal irrigation fluid exit opening 72, the distal irrigation fluid entry opening 74 or the irrigation fluid inlet opening and the irrigation fluid outlet opening closes or impairs or unintentionally firmly cements the first connecting means 58 or the second connecting means 59 on the tibia prosthetic body.

Figure 12:
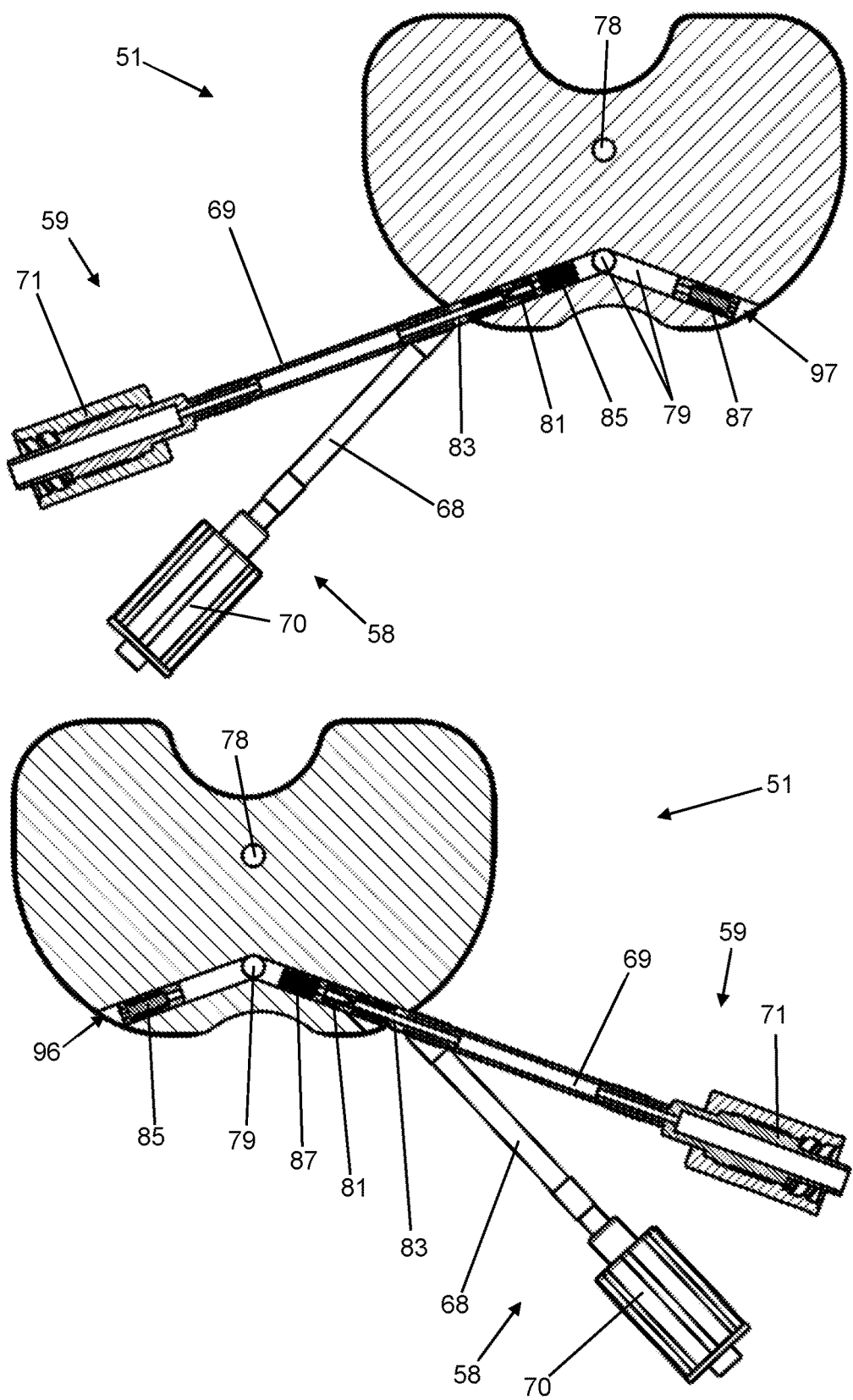
FIG. 12: shows two profile views along a transverse plane of the tibia component according to FIGS. 9 to 11.
Figure 13:
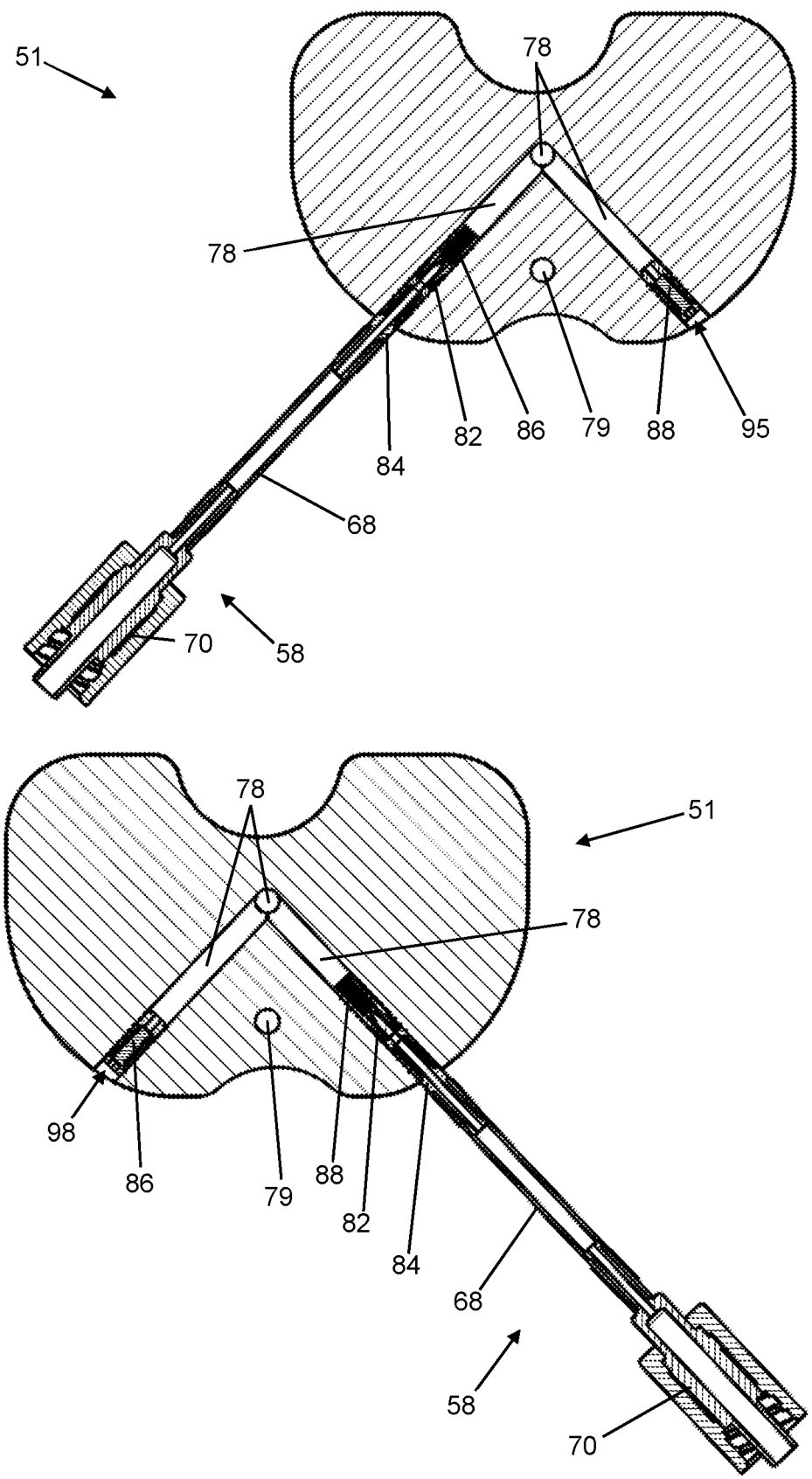
FIG. 13: shows two further profile views along a transverse plane of the tibia component parallel to FIG. 12 according to FIGS. 9 to 12.
Figure 14:
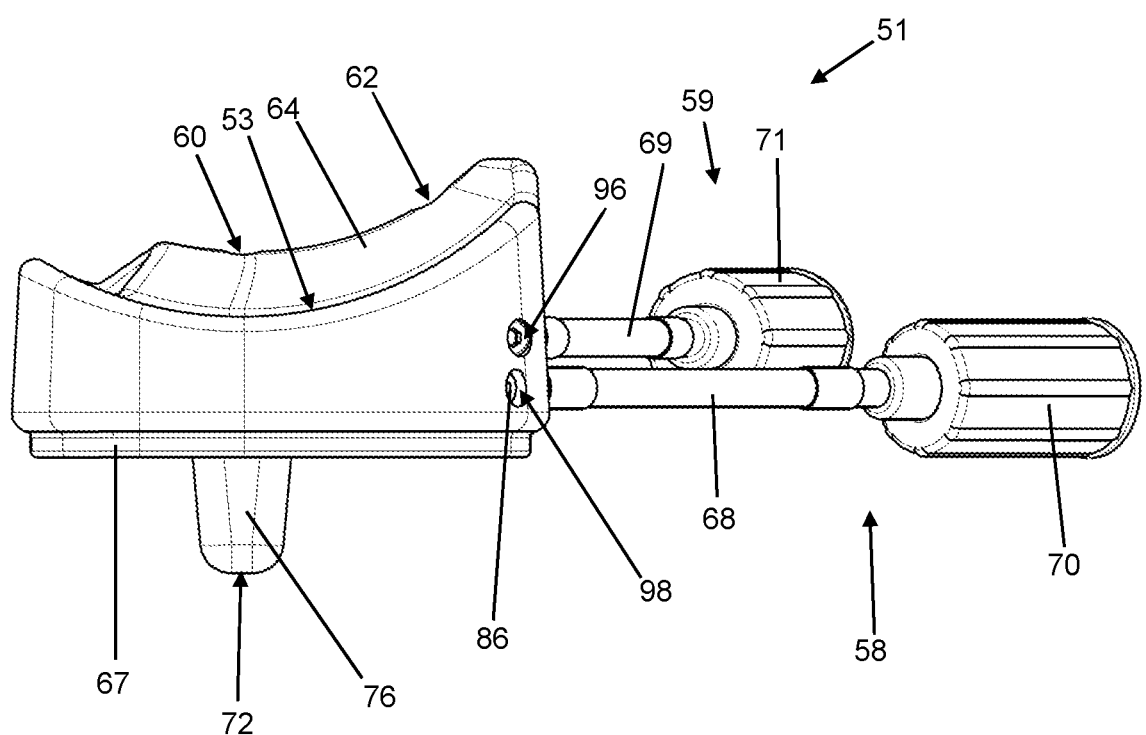
FIG. 14: shows a schematic side view onto a lateral side of the tibia component according to FIGS. 8 to 13.
Figure 15:
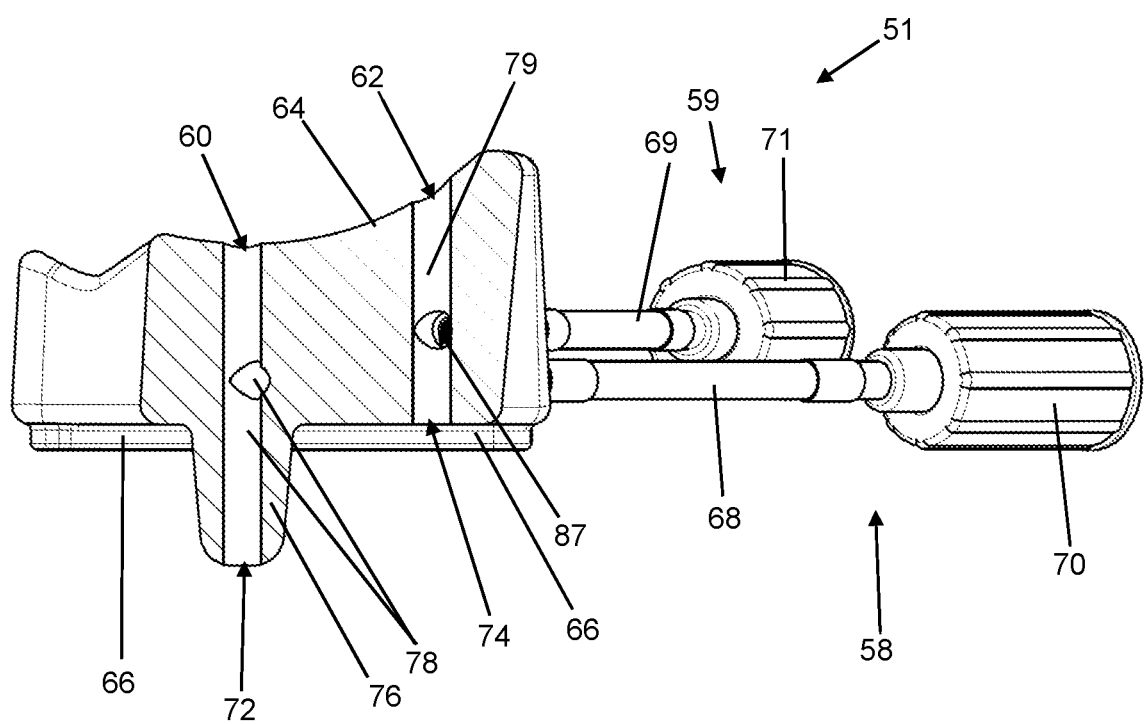
FIG. 15: shows a side profile view along a sagittal plane of the tibia component according to FIGS. 8 to 14.

In the profile views shown in FIGS. 12, 13 and 15, it can largely be seen how the irrigation fluid outlet opening with the proximal irrigation fluid entry opening 62 and the distal irrigation fluid entry opening 74 and the irrigation fluid inlet opening are connected to the proximal irrigation fluid exit opening 60 and the distal irrigation fluid exit opening 72 in the interior of the tibia prosthetic body. The tibia prosthetic body is essentially made from plastic. Preferably from a bone cement, such as a PMMA plastic, which can be charged with an antibiotic or with several antibiotics.

In the interior of the tibia prosthetic body, the irrigation fluid inlet opening is connected to the proximal irrigation fluid exit opening 60 and the distal irrigation fluid exit opening 72 via a first line 78. The first line 78 creates a fluid-permeable connection between the irrigation fluid inlet opening and the proximal irrigation fluid exit opening 60 and the distal irrigation fluid exit opening 72. For this purpose, in the interior of the tibia prosthetic body, a branch in the form of a T-piece is provided in the first line 78 (see FIGS. 12, 13 and 15). Equally, in the interior of the prosthetic body, the irrigation fluid outlet opening is connected to the proximal irrigation fluid entry opening 62 and the distal irrigation fluid entry opening 74 via a second line 79. The second line 79 also comprises a branch for this purpose in the form of a T-piece. The first line 78 and the second line 79 are separated from each other in the interior of the tibia prosthetic body.

On an end of the first connecting means 58 for feeding an irrigation fluid, opposite the Luer lock adapter 20, a first valve element 82 is arranged on a connecting element 84, which permits a feed of medical irrigation fluid from the first connecting means 58 into the first line 78 and into the tibia prosthetic body, and which prevents a return flow from the first line 78 into the connecting means 58. Equally, on an end of the second connecting means 59 for discharging an irrigation fluid, opposite the Luer lock adapter 71, a second valve element 81 is provided in a second connecting element 83, which permits a discharge of fluid from the second line 79 into the second connecting means 59, and which prevents a return flow from the hose 69 into the second line 79. The first exemplary embodiment according to FIGS. 1 to 6 thus also differs from the second exemplary embodiment according to FIGS. 8 to 15 due to the arrangement of the valve elements 81, 82 in the connecting means 58, 59.

The second connecting means 59 is connected or connectable via the detachable connecting element 83 with each of the irrigation fluid outlet openings 96, 97 and, if desired, is also connectable with each of the irrigation fluid inlet openings 95, 98. In the same manner, the first connecting means 58 is connected or connectable via the detachable connecting element 84 with each of the irrigation fluid inlet openings 95, 98 and, if desired, is also connectable with each of the irrigation fluid outlet openings 96, 97. In order to connect the first connecting means 58 with the tibia prosthetic body, in the first line 78 in the area of the first irrigation fluid inlet opening 95, a first counter-fastening element 88 is arranged, and in the area of the second irrigation fluid inlet opening 98, a second counter-fastening element 86 is arranged. In the same manner, in order to connect the second connecting means 59 with the tibia prosthetic body, in the second line 79 in the area of the first irrigation fluid inlet opening 96, a third counter-fastening element 85 is arranged, and in the area of the second irrigation fluid outlet opening 97, a fourth counter-fastening element 87 is arranged. The connecting elements 83, 84 can be attached or are attached to one of the counter-fastening elements 85, 86, 87, 88 via an outer thread. The attachment can be realized via threads, for example, or also via a bayonet connection or a plug-in connection. The first connecting means 58 and the second connecting means 59 can thus be detached by the detachable connecting elements 83, 84 being pulled off or unscrewed from the tibia prosthetic body. The counter-fastening elements 85, 86, 87, 88 designed such that they automatically close the irrigation fluid outlet openings 96, 97 and the irrigation fluid inlet openings 95, 98 when the connecting means 83, 84 are detached.

The femur component 52 has several mounting surfaces 92 on its proximal side, which are interrupted by ridges 91. The mounting surfaces 92 serve to connect the femur component 52 with the femur, whereby a bone cement connects the mounting surfaces 92 with the femur. The ridges 91 protrude in the proximal direction from the proximal surface of the femur component 52. Alternatively, the femur component 2 can also be used according to FIG. 7 in order to realize a knee spacer system according to the invention.

On the distal side, the femur component 52 has two adjacent condyles 93, 94. The condyles 93, 94 can roll on the running surfaces of the tibia component 51, so that the femur component 52 and the tibia component 51 together form a knee spacer system according to the invention.

According to a further embodiment of the present invention not shown in the Figures, the femur component can also be fitted with an irrigation device. For this purpose, similar to the tibia component 1, 51, a suitable feed for the medical irrigation fluid and a suitable discharge for the irrigation fluid is required, and at least one irrigation fluid entry opening and at least one irrigation fluid exit opening similar to the tibia component 1, 51, which are separated from each other via lines and which are connected with the feed or the discharge line. Preferably, the feeds and discharges of the tibia component 1, 51 and the rinseable femur component (not shown) are kept separate.

The features of the invention disclosed in the above description and in the Claims, Figures and exemplary embodiments, can be essential both individual and in any combination required for the realization of the invention in its different embodiments.

LIST OF REFERENCE NUMERALS

1, 51 Tibia component
2, 52 Femur component 3, 53 Running surface
4, 54 Running surface
5, 55 Mounting surface
6, 56 Mounting surface
8, 58 Connecting means for feeding an irrigation fluid
9, 59 Connecting means for discharging an irrigation fluid
10, 60 Irrigation fluid exit opening
12, 62 Irrigation fluid entry opening
14, 64 Bridge
16, 66 Ridge
17, 67 Ridge
18, 68 Hose
19, 69 Hose
20, 70 Luer lock adapter
21, 71 Luer lock adapter
22, 72 Irrigation fluid exit opening
24, 74 Irrigation fluid entry opening
26, 76 Distal protrusion
28, 78 Line
29, 79 Line
31, 81 Valve element
32, 82 Valve element
33, 83 Connecting element
34, 84 Connecting element
35 Counter-fastening element
41, 91 Ridge
42, 92 Mounting surface
43, 93 Condyle
44, 94 Condyle
85, 87 Counter-fastening element
86, 88 Counter-fastening element
95, 98 Irrigation fluid inlet opening
96, 97 Irrigation fluid outlet opening

The invention claimed is:

1. A knee spacer system for the temporary replacement of a knee joint, the knee spacer system comprising:
a tibia component, wherein the tibia component has a tibia prosthetic body, wherein the tibia prosthetic body has two running surfaces on a proximal side of the tibia component and at least one mounting surface for mounting the tibia component on a tibia on a distal side of the tibia prosthetic body;
a first tubular and fluid-permeable connecting means for feeding a medical irrigation fluid into the tibia prosthetic body;
a second tubular and fluid-permeable connecting means for draining a medical irrigation fluid from the tibia prosthetic body;
an irrigation fluid inlet opening in a surface of the tibia prosthetic body, wherein the first connecting means is connected or connectable in a fluid-permeable manner to the irrigation fluid inlet opening;
an irrigation fluid outlet opening in the surface of the tibia prosthetic body, wherein the second connecting means is connected or connectable in a fluid-permeable manner to the irrigation fluid outlet opening;
at least one irrigation fluid exit opening in the surface of the tibia prosthetic body, which is connected in the interior of the tibia prosthetic body with the irrigation fluid inlet opening in a fluid-permeable manner; and
at least one irrigation fluid entry opening in the surface of the tibia prosthetic body, which is connected in the interior of the tibia prosthetic body with the irrigation fluid outlet opening in a fluid-permeable manner,
wherein the at least one irrigation fluid exit opening and the at least one irrigation fluid entry opening are arranged outside the at least one mounting surface, and wherein the at least one irrigation fluid exit opening in the interior of the prosthetic body is not connected in a fluid-permeable manner with the irrigation fluid outlet opening and the at least one irrigation fluid entry opening in the interior of the prosthetic body is not connected with the irrigation fluid inlet opening in a fluid-permeable manner.

2. The knee spacer system of claim 1, wherein the at least one mounting surface is bound by a surrounding ridge that rises from the surface of the tibia prosthetic body, so that the at least one mounting surface is suitable for holding bone cement paste within the ridge.

3. The knee spacer system of claim 1, wherein the tibia component has at least two irrigation fluid exit openings and at least two irrigation fluid entry openings in the surface of the tibia prosthetic body, which are arranged on different sides of the tibia prosthetic body.

4. The knee spacer system of claim 3, wherein an irrigation fluid exit opening and an irrigation fluid entry opening are arranged on the proximal side of the tibia prosthetic body and an irrigation fluid exit opening and an irrigation fluid entry opening are arranged on the distal side of the tibia prosthetic body.

5. The knee spacer system of claim 1, wherein the at least one irrigation fluid exit opening and the at least one irrigation fluid entry opening are spaced apart from each other in pairs, wherein the space between each pair of the at least one irrigation fluid exit opening and the at least one irrigation fluid entry opening is at least 5 mm, preferably at least 20 mm and particularly preferably, at least 30 mm.

6. The knee spacer system of claim 1, wherein the first connecting means on the side facing away from the connection with the irrigation fluid inlet opening and the second connecting means on the side facing away from the connection with the irrigation fluid outlet opening each has one adapter, in particular each has a Luer lock adapter.

7. The knee spacer system of claim 1, wherein at the irrigation fluid inlet opening in the interior of the tibia prosthetic body or on the surface of the tibia prosthetic body, a self-sealing coupling is arranged, and at the irrigation fluid outlet opening in the interior of the tibia prosthetic body or on the surface of the tibia prosthetic body, a self-sealing coupling is arranged, wherein the first connecting means is detachably connected or connectable with the irrigation fluid inlet opening and the second connecting means is detachably connected or connectable with the irrigation fluid outlet opening.

8. The knee spacer system of claim 1, wherein the irrigation liquid inlet opening is a first irrigation liquid inlet opening, and the irrigation liquid outlet opening is a first irrigation liquid outlet opening, wherein additionally, a second irrigation liquid inlet opening and a second irrigation liquid outlet opening are provided in the surface of the tibia prosthetic body, wherein at each of the first irrigation liquid inlet opening, the second irrigation liquid inlet opening, the first irrigation liquid outlet opening and the second irrigation liquid outlet opening, one self-sealing coupling is arranged, wherein the first connecting means is connectable in a fluid-tight and detachable manner with the first irrigation liquid inlet opening and with the second irrigation liquid inlet opening, and the second connecting means is connectable in a fluid-tight and detachable manner with the first irrigation liquid outlet opening and with the second irrigation liquid outlet opening, wherein
the first irrigation liquid inlet opening and the second irrigation liquid inlet opening are connected in a fluid-permeable manner with each other in the tibia prosthetic body, and the first irrigation liquid outlet opening and the second irrigation liquid outlet opening are connected in a fluid-permeable manner with each other in the tibia prosthetic body.

9. The knee spacer system of claim 8, wherein the first irrigation liquid inlet opening and the first irrigation liquid outlet opening are arranged on a first side of the tibia component in relation to a sagittal plane, and the second irrigation liquid inlet opening and the second irrigation liquid outlet opening is arranged on a second side of the tibia component in relation to the sagittal plane.

10. The knee spacer system of claim 9, wherein the first irrigation liquid inlet opening and the first irrigation liquid outlet opening are arranged in relation to the sagittal plane in a mirror-inverted manner to the second irrigation liquid inlet opening and to the second irrigation liquid outlet opening in the surface of the tibia prosthetic body.

11. The knee spacer system of claim 1, wherein a cross-sectional area of the at least one irrigation liquid entry opening is at least just as large as a cross-sectional area of the irrigation liquid inlet opening.

12. The knee spacer system of claim 1, wherein the total of cross-sectional areas of the at least one irrigation liquid exit opening is at least just as large as a cross-sectional area of the irrigation liquid outlet opening.

13. The knee spacer system of claim 1, wherein the at least one irrigation liquid exit opening and the at least one irrigation liquid entry opening are separated from the at least one mounting surface by a surrounding ridge that rises from the surface of the prosthetic body.

14. The knee spacer system of claim 1, wherein at least one irrigation fluid exit opening of the at least one irrigation fluid exit opening and/or at least one irrigation fluid entry opening of the least one irrigation fluid entry opening is or are arranged between the running surfaces.

15. The knee spacer system of claim 1, wherein the at least one irrigation fluid exit opening and the at least one irrigation fluid entry opening are arranged outside the running surfaces.

16. The knee spacer system of claim 1, wherein one irrigation fluid exit opening of the at least one irrigation fluid exit opening and one irrigation fluid entry opening of the least one irrigation fluid entry opening are arranged adjacent to one of the running surfaces, preferably within 3 mm adjacent to one of the running surfaces.

17. The knee spacer system of claim 1, wherein in the first connecting means or in the irrigation fluid inlet opening, a first valve element is arranged that prevents a return flow of the irrigation fluid into the first connecting means.

18. The knee spacer system of claim 1, wherein in the second connecting means or in the irrigation fluid outlet opening, a second valve element is arranged that prevents a return flow of the irrigation fluid into the second connecting means.

19. The knee spacer system of claim 18, wherein the first and second valve element are selected from a non-return valve, a ball valve with spring, a lip valve, a Bunsen valve or a plate valve.

20. The knee spacer system of claim 1, wherein in a first line within the tibia prosthetic body, which connects the at least one irrigation fluid entry opening with the irrigation fluid outlet opening in a fluid-permeable manner, a first valve is arranged which can only be opened by applying negative pressure to the irrigation fluid outlet opening, and which prevents a return flow of the irrigation fluid into the first line.

21. The knee spacer system of claim 1, wherein in a second line within the tibia prosthetic body, which connects the at least one irrigation fluid exit opening with the irrigation fluid inlet opening in a fluid-permeable manner, a second valve is arranged which can only be opened by applying negative pressure to the irrigation fluid inlet opening, and which prevents a return flow of the irrigation fluid into the second line.

22. The knee spacer system of claim 1, wherein in the tibia prosthetic body, the irrigation fluid inlet opening, the irrigation fluid outlet opening, the at least one irrigation fluid exit opening and the at least one irrigation fluid entry opening and the fluid-permeable connections are formed.

23. The knee spacer system of claim 1, wherein the tibia prosthetic body is preferably made of plastic, metal, ceramic, glass ceramic, bone cement or a combination of these.

24. The knee spacer system of claim 1, wherein the irrigation fluid inlet opening and the irrigation fluid outlet opening are arranged in a side surface of the tibia prosthetic body or on a lateral side surface of the tibia prosthetic body.

25. The knee spacer system of claim 1, wherein at least one first irrigation fluid exit opening of the at least one irrigation fluid exit opening is arranged on the proximal side in the surface of the tibia prosthetic body, and at least one second irrigation fluid exit opening of the at least one irrigation fluid exit opening is arranged on the distal side in the surface of the tibia prosthetic body, and at least one first irrigation fluid entry opening of the at least one irrigation fluid entry opening is arranged on the proximal side in the surface of the tibia prosthetic body, and at least one second irrigation fluid entry opening of the at least one irrigation fluid entry opening is arranged on the distal side in the surface of the tibia prosthetic body.

26. The knee spacer system of claim 1, wherein the knee spacer system has a femur component, wherein the femur component has two condyles on one distal side.

27. The knee spacer system of claim 26, wherein the femur component has a femur prosthetic body, wherein the femur prosthetic body has at least one mounting surface for mounting the femur component with a bone cement to a femur on one proximal side of the femur prosthetic body, the femur component further comprising:
 a third tubular and fluid-permeable connecting means for feeding a medical irrigation fluid into the femur prosthetic body;
 a fourth tubular and fluid-permeable connecting means for draining a medical irrigation fluid from the femur prosthetic body;
 an irrigation fluid inlet opening in a surface of the femur prosthetic body, wherein the third connecting means is connected or connectable in a fluid-permeable manner to the irrigation fluid inlet opening of the femur prosthetic body;
 an irrigation fluid outlet opening in a surface of the femur prosthetic body, wherein the fourth connecting means is connected or connectable in a fluid-permeable manner to the irrigation fluid outlet opening of the femur prosthetic body;
 at least one irrigation fluid exit opening in the surface of the femur prosthetic body, which is connected in the interior of the femur prosthetic body with the irrigation fluid inlet opening of the femur prosthetic body in a fluid-permeable manner; and
 at least one irrigation fluid entry opening in the surface of the femur prosthetic body, which is connected in the interior of the femur prosthetic body with the irrigation fluid outlet opening of the femur prosthetic body in a fluid-permeable manner, wherein the at least one irrigation fluid exit opening of the femur prosthetic body and the at least one irrigation fluid entry opening of the femur prosthetic body are arranged outside the at least one mounting surface of the femur prosthetic body.

28. The knee spacer system of claim 27, wherein the at least one irrigation fluid exit opening of the femur prosthetic body and the at least one irrigation fluid entry opening of the femur prosthetic body are arranged outside the condyles of the femur prosthetic body.

29. The knee spacer system of claim 1, wherein at least one irrigation fluid exit opening of the at least one irrigation fluid exit opening or at least one irrigation fluid entry opening of the least one irrigation fluid entry opening is arranged on a distal side of a protrusion extending in the distal direction between two mounting surfaces of the tibia component.

* * * * *